United States Patent
Davis, Jr. et al.

(10) Patent No.: US 10,545,113 B2
(45) Date of Patent: Jan. 28, 2020

(54) ELECTROCHEMICAL DETECTION METHOD

(71) Applicants: Oxford University Innovation Limited, Oxford (GB); Universidade Estadual Paulista "Julio de Mesquita Filho", Centro, Sao Paulo (BR)

(72) Inventors: Jason Davis, Jr., Oxford (GB); Paulo Roberto Bueno, Sao Paulo (BR)

(73) Assignees: ISIS Innovation Limited (GB); Universidade Estadual Paulista "Julio de Mequita Filho" (BR)

(*) Notice: Subject to any disclaimer, the term of this patent is extended or adjusted under 35 U.S.C. 154(b) by 427 days.

(21) Appl. No.: 14/398,211

(22) PCT Filed: May 1, 2013

(86) PCT No.: PCT/GB2013/051124
§ 371 (c)(1),
(2) Date: Oct. 31, 2014

(87) PCT Pub. No.: WO2013/164613
PCT Pub. Date: Nov. 7, 2013

(65) Prior Publication Data
US 2015/0090609 A1   Apr. 2, 2015

(30) Foreign Application Priority Data
May 1, 2012 (GB) .................................. 1207583.4

(51) Int. Cl.
G01N 33/48 (2006.01)
G01N 31/00 (2006.01)
G01N 27/327 (2006.01)

(52) U.S. Cl.
CPC ................................ *G01N 27/327* (2013.01)

(58) Field of Classification Search
None
See application file for complete search history.

(56) References Cited

U.S. PATENT DOCUMENTS 6,413,410 B1 * 7/2002 Hodges .................. C12Q 1/004
 205/775
6,824,669 B1 * 11/2004 Li ...................... G01N 33/5438
 204/403.01

(Continued)

FOREIGN PATENT DOCUMENTS

JP 60064242 4/1985
JP 2003202321 A 7/2003

(Continued)

OTHER PUBLICATIONS

Yang, L.C. et al, "Direct Electrical Transduction of Antibody Binding to a Covalent Virus Layer Using Electrochemical Impedance," Anal. Chem., vol. 80, 2008, pp. 5695-5705.

(Continued)

*Primary Examiner* — Anna Skibinsky
(74) *Attorney, Agent, or Firm* — Banner & Witcoff, Ltd.

(57) ABSTRACT

Electrochemical detection method and related aspects Herein is disclosed an electrochemical test method comprising (i) comparing how a plurality of immittance functions and/or components thereof vary with a change in a parameter of interest for a first system, and then selecting an immittance function or component thereof for use in an electrochemical test; (ii) carrying out an electrochemical test step for a second system to determine at least one value for the immittance function or component thereof selected in step (i), and then, by using a quantitative relationship between the selected immittance function and the parameter of interest, determining a value in the parameter of interest. A computer program and apparatus are also disclosed herein.

8 Claims, 15 Drawing Sheets

(56) References Cited

U.S. PATENT DOCUMENTS

| | | | |
|---|---|---|---|
| 7,711,402 B2* | 5/2010 | Shults | A61B 5/14532 600/347 |
| 2005/0069892 A1* | 3/2005 | Iyengar | G01N 27/3273 435/6.12 |
| 2008/0000780 A1* | 1/2008 | Tonks | G01N 27/3274 205/792 |
| 2010/0234234 A1 | 9/2010 | Ko Ferrigno et al. | |
| 2010/0234237 A1* | 9/2010 | Yoo | B01L 3/50273 506/9 |
| 2011/0224914 A1 | 9/2011 | Messing | |
| 2013/0199944 A1* | 8/2013 | Petisee | A61B 5/1486 205/778 |

FOREIGN PATENT DOCUMENTS

| | | |
|---|---|---|
| WO | 0055639 A1 | 9/2000 |
| WO | 2007143786 A1 | 12/2007 |
| WO | 2011069997 A2 | 6/2011 |

OTHER PUBLICATIONS

Macdonald, J.R. "Impedance Spectroscopy: Old Problems and New Developments," Electrochimica Acta, vol. 35, No. 10, 1990, 1483-1492.

Scholle et al., Sequence of the mgIB gene from *Escherichia coli* K12: Comparison of wild-type and mutant galactose chemoreceptors, Mol. Gen. Genet, 1987, vol. 208, 247-253.

Motheo, A.J. et al., Electrochemical Immittance Spectroscopy Applied to the Study of the Single Crystal Gold/Aqueous Perchloric Acid Interface, Electrochemical Chemistry, Jan. 1, 1997, 253-262.

Macdonald, J.R. "Some New Directions in Impedance Spectroscopy Data Analysis," Electrochimica Acta, vol. 38, No. 14, Oct. 1, 1993, 1883-1890.

Aug. 17, 2012—(GB) Search Report—App No. GB1207583.4—3 pages.

Jul. 3, 2013—(WO) International Search Report and Written Opinion—App. No. PCT/GB2013/051124—11 pages.

* cited by examiner

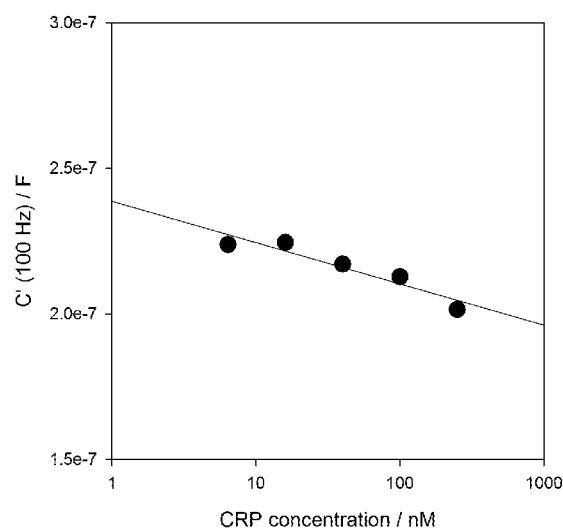 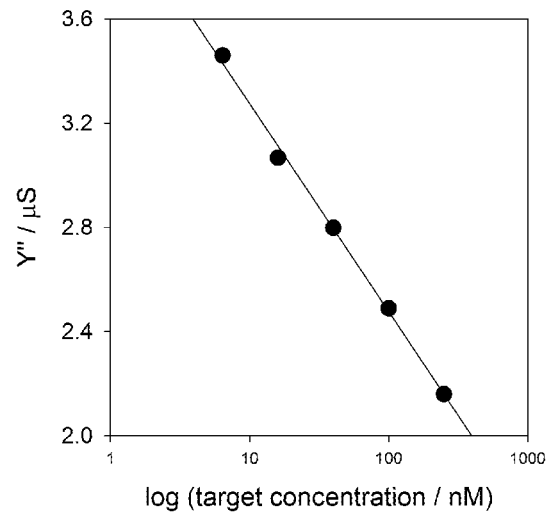
Fig. 6A
Fig. 6B

ELECTROCHEMICAL DETECTION METHOD

CROSS REFERENCE TO RELATED APPLICATIONS

This application is a National Stage Application under 35 U.S.C. 371 of co-pending PCT application number PCT/GB2013/051124, filed 1 May 2013; which claims priority to GB1207583.4, filed 1 May 2012, each of which are hereby incorporated by reference in their entireties.

BACKGROUND

The detection and quantification of protein biomarkers in biological samples lies central to proteomics, drug design, disease prognosis and therapeutic development. The generation of viable protein microarrays is, though, challenging. Current antibody based optical microarrays are commonly based on sandwich assays in which antigen binding to the immobilised antibody is detected through the use of a secondary, labeled, antibody. Though sensitive, this method is laborious and requires a specifically-labeled secondary antibody for every antigen of interest. Labeling protocols are potentially perturbative, can also be time consuming and may lead to high background signals. Label free detection assays based on plasmon resonance or quartz crystal microbalance (QCM), for example, offer, typically, nM detection limits but require the use of sophisticated and very expensive pieces of equipment.

Other techniques using electrochemical principles have also been developed for assays. Assays are generated by controllably immobilizing receptive biomolecules (typically antibodies, nucleic acids or peptides) on electrodes and converting the target protein binding event into a measurable electrical signal. One of the most sensitive and powerful means of doing this is by impedance; that is through the application of a sinusoidal voltage to the supporting electrode and the measurement of the resulting current. Though it can be exceedingly sensitive, the measurement of impedance is that of only one interfacial electrical parameter and furthermore, is commonly interpreted only through the application of an "assumed equivalent circuit". There are a variety of assumed equivalent circuits, and they are used to approximate the electrochemical interface (e.g. at the surface of a working electrode). Generally, the most appropriate assumed equivalent circuit must be chosen or devised to correctly interpret the data. For this to be successful, it requires a considerable degree of knowledge of the electrochemistry at the relevant electrochemical interface.

The present invention aims to provide an alternative to, ideally an improvement upon, the methods of the prior art. For example, it would be desirable to be able to calculate the concentration of biomolecules in solution at high accuracy using impedance data, but without having to interpret the data using an assumed equivalent circuit.

BRIEF DESCRIPTION OF THE FIGURES

FIG. 6A shows the variance of the real part of capacitance immittance function with CRP concentration for a receptive interface; data obtained at a sampling frequency of 1 Hz, where $R_{ct}$ and z' are most correlated as shown in FIG. 8.

FIG. 6B shows an analytical curve of Y" versus logarithmic target (CRP) concentration. Variations are ~45% across the same target concentration range.

SUMMARY OF THE INVENTION

Figure 1:
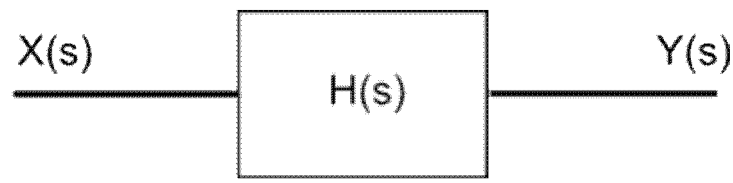
FIG. 1 shows in schematic form a definition of a transfer function. The function, H(s), is applied over a linear time invariant system (LTIS).
Figure 2:
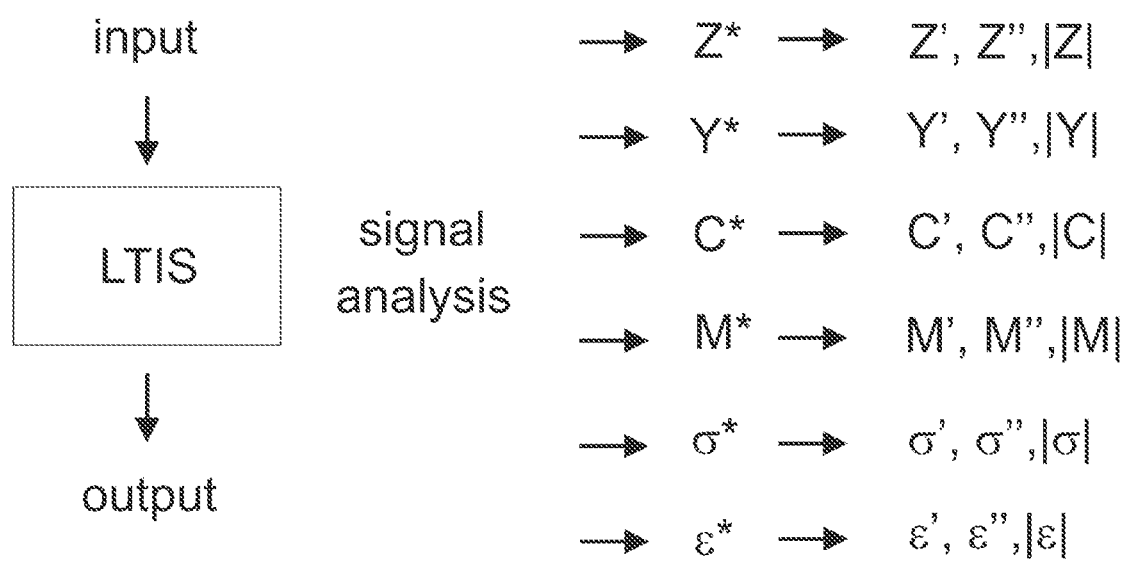
FIG. 2 shows schematically how a signal can be treated to generate a set of complex immittance functions (centre) and a subset of immittance function components (right).

The present invention provides, in a first aspect, an electrochemical test method comprising
(i) comparing how a plurality of immittance functions and/or components thereof vary with a change in a parameter of interest for a first system, and then selecting an immittance function or component thereof for use in an electrochemical test;
(ii) carrying out an electrochemical test step for a second system to determine at least one value for the immittance function or component thereof selected in step (i), and then, by using a quantitative relationship between the selected immittance function and the certain parameter, determining a value in the parameter of interest. The electrochemical test step may comprise or be an electrochemical assay.

The present invention provides, in a second aspect, a computer program for use in a method comprising
comparing how a plurality of immittance functions and/or components thereof vary with a change in a parameter of interest for a first system, and then selecting an immittance function.

The present invention provides, in a third aspect, an apparatus for use in an electrochemical test method, wherein the apparatus is adapted to carrying out the electrochemical method according to the first aspect.

The present inventors have found that when carrying out electrochemical tests, different immittance functions and their components vary to different extents when a parameter of interest is altered. Furthermore, they have found that, in contrast to standard electrochemical impedance spectroscopy (EIS) techniques, there is no requirement to use equivalent circuit models in an attempt to model the system of interest. The various immittance functions or their components can simply be plotted against the parameter of interest (or its logarithm) and the variation over a range of the parameter of interest can be determined. The present inventors have also found that they can use relationships between different immittance functions to easily generate a library of immittance functions and how they vary with the parameter of interest, and then use that in test methods. The method also allows the linear and/or dynamic range of an assay to be extended by using different immittance functions for different ranges of a parameter.

Immittance and Transfer Functions

Immittance and transfer functions will first be described.

An immittance function in the present application is an electrochemical transfer function. Unless otherwise indicated, an immittance function is the combination of its real and imaginary parts, sometimes termed a complex immittance function. A component of an immittance function can include the real part of the immittance function, the imaginary part of the immittance function, the amplitude of an immittance function and the phase of the immittance function. An immittance function is generated by applying either a varying, typically a sinusoidal, voltage or current between a working electrode and a counter electrode, then measuring the response, i.e. either the current or voltage, respectively; an immittance function represents a relationship between the applied voltage or current and the resulting current or voltage, respectively. The applied voltage or current varies with a predetermined frequency and the resulting current or voltage typically has the same frequency, but a different phase. Because of this phase difference between the applied voltage or current, and the resulting current or voltage, the relationship can be expressed in complex terms, i.e. with a real part (or component) and an imaginary part or component. This is explained in more details below with reference to transfer functions.

Transfer functions (TFs) have been used in the analysis of systems such as single-input single-output filters, typically within the fields of signal processing, communication theory, and control theory. A transfer function is a mathematical representation, in terms of spatial or temporal frequency, of the relation between the input and output of a Linear Time-invariant System (LTIS). With optical imaging devices, for example, it is the Fourier transform of the point spread function (hence a function of spatial frequency), i.e. the intensity distribution caused by a point object in the field of view.

Linearity is a mathematical constraint that allows the conversion of time into frequency domain, meaning that the perturbation on the system must be very small and time independent of the response. The time independent constraint is related to the fact that steady state feature of the system during the perturbation should be maintained. Practically, in order to ensure the linearity constraint applies a small oscillatory perturbation (i.e. varying voltage or current) is generally used during the signal acquisition.

The transfer function of a process or system is characteristic of its dynamic behavior. To get the dynamic behavior of the system as a fingerprint, a constraint must be imposed, namely in keeping the system at steady state (assured by the linearity in the ratio between the input and output signal).

FIG. 1 illustrates schematically the definition of a transfer function. In this figure, X(s) represents an input signal, Y(s) represents an output signal, and H(s) is the transfer function applied to X(s) to give Y(s). The H(s) is applied over a linear time invariant system.

In its simplest form for continuous-time input signal x(t) and output y(t), the transfer function is the linear mapping of the Laplace transform $L\{\ \}$ of the input, X(s), to the output Y(s) so that $$Y(s) = H(s)X(s)$$

or $$H(s) = \frac{Y(s)}{X(s)} = \frac{\mathcal{L}\{y(t)\}}{\mathcal{L}\{x(t)\}}$$

where H(s) is the transfer function of the LTIS and $$X(s) = L\{x(t)\} = \int_{-\infty}^{\infty} x(t)e^{-st}dt \quad \text{(mathematical definition)}$$

$$Y(s) = L\{y(t)\} = \int_{-\infty}^{\infty} y(t)e^{-st}dt \quad \text{(mathematical definition)}$$

In particular, if a complex harmonic signal with a sinusoidal component with amplitude X(s), angular frequency ω and phase arg(X)

$$x(t) = Xe^{j\omega t} = |X|e^{j(\omega t + \arg(X))}$$

where $X = |X|e^{j\,\arg(X)}$
is the input to a linear time-invariant system, such that the corresponding output is:

$$y(t) = Ye^{j\omega t} = |Y|e^{j(\omega t + \arg(Y))}$$

where $Y = |Y|e^{j\,\arg(Y)}$.

Note that, in a linear time-invariant system, the input frequency ω of the sinusoidal perturbation (e.g. the applied voltage or current in the context of the present application) is unchanged across or by the timeline of the signal analysis, only the amplitude and the phase angle of the output signal sinusoid is modulated by the system under analysis. The frequency response $H(\omega)$ describes this change for every input frequency $\omega$ in terms of gain:

$$G(\omega) = \frac{|Y|}{|X|} = |H(j\omega)|$$

and phase shift:

$$\phi(\omega) = \arg(Y) - \arg(X) = \arg(H(j\omega))$$

The phase delay (i.e., the offset between the phase of the input and the detected phase of the output by the transfer function) is:

$$\tau_\phi(\omega) = -\frac{\phi(\omega)}{\omega}$$

The group delay (i.e., the frequency-dependent amount of delay introduced to the envelope of the sinusoid by the transfer function) is found by computing the derivative of the phase shift with respect to angular frequency $\omega$, $$\tau_g(\omega) = -\frac{\phi(\omega)}{\omega}$$

The transfer function $H(\omega)$ can also be derived using the Fourier transform as well as Laplace transform for the case where $s=j\omega$, where $j=\sqrt{-1}$.

Impedance Signal Analysis

Impedance can be identified as the particular transfer function in the case of the input signal being a modulated potential $V(t)=\bar{V}+\tilde{V}e^{j\omega t}$ (in which $\bar{V}$ is a steady state potential over which the perturbation is done and $\tilde{V}$ is the amplitude of the potential perturbation) and an output the response in current $I(t)=\bar{I}+\tilde{I}e^{(j\omega t-\phi)}$, resulting in the complex impedance immittance function $Z^*(\omega)$, i.e. a complex transfer function:

$$Z^*(\omega) = \frac{\tilde{V}}{\tilde{I}} \frac{e^{j\omega t}}{e^{(j\omega t-\phi)}} = |Z|e^{j\phi}$$

The steady state potential, $\bar{V}$, is sometimes termed a DC potential, and the applied varying potential is sometimes termed the AC potential, which has the amplitude $\tilde{V}$ and frequency $\omega$.

The $Z^*(\omega)$ complex function is dissolvable into two constituent components $$Z^*(\omega) = Z' + jZ''$$

where $Z'$ and $Z''$ are, respectively, the real and imaginary parts (or the real and imaginary components) of the impedance transfer function. $|Z|$ is known as the modulus and is mathematically related to $Z'$ and $Z''$ ($|Z|^2 = Z'^2 + Z''^2$).

These terms ($Z'$ and $Z''$) can be related graphically in Nyquist diagrams. Standard impedance analyses (also known as Electrochemical Impedance Spectroscopy, EIS) report the set of $Z''$, $Z'$, $|Z|$ terms and the associated phase $\phi$, using Nyquist diagrams or Bode representation of these terms. $\phi$ is mathematically related to $Z'$ and $Z''$ by $\phi = \tan^{-1}(Z''/Z')$.

In an embodiment, the amplitude of the applied ac potential, which is typically in the form of a sine wave, may be a value of from 1 mV to 100 mV. The steady state potential may be any desired potential, and can be selected by the skilled person. In an embodiment, the steady state potential has a magnitude of at least 0.1 V (relative to Ag/AgCl), and may be a negative or positive potential.

Sometimes in prior art methods, using an equivalent circuit approach, the data set can be fitted and processed to attribute physical meaning to the derived fitting terms such as capacitance and resistance (components of an assumed "equivalent circuit"). Typically, in these prior art methods, it is only these terms, or functions, that are resolved (i.e. $Z''$, $Z'$, $|Z|$, $\phi$ and circuit components).[1] The fitting process itself can also be highly problematic. (see, for example, J. R. Macdonald, IMPEDANCE SPECTROSCOPY: OLD PROBLEMS AND NEW DEVELOPMENTS, Electrochimica Acta, Vol. 35, No. 10, pp. 1483-1492, 1990, which is incorporated herein by reference in its entirety).

Any sensorial technology based on above picture of EIS has associated these constraints and, in many cases, both a pre-determined hardware configuration and assumed outcome.

From the above, it is important to note that impedance is a specific form of transfer function in the case of voltage and current input/output signal analysis. From a modulated potential $V(t)=\bar{V}+\tilde{V}e^{j\omega t}$ input signal and an output sigmoidal response in current $I(t)=\bar{I}+\tilde{I}e^{(j\omega t-\phi)}$. As explained below, the present inventors have found that by generating a plurality of immittance functions for a system, and then determining how the immittance functions and/or their components vary with a parameter of interest (e.g. concentration of a target species), it is possible to select the most appropriate immittance function or component for carrying out a subsequent test. In this subsequent test where the parameter of interest is not known initially, a value for the selected immittance function or immittance function component is determined, and then used to convert to a value in the parameter of interest.

The present inventors have found that a whole library of immittance functions and their relationships, can, in fact, be derived (see below), without having to resort to equivalent circuit fitting. They have found that some immittance functions are more sensitive to highly specific interfacial changes than others. There are considerable advantages in acquiring and processing such a library, and it avoids being tied to one sampling function and having to assume anything about the best function to follow or circuit to fit data to.

Determining Immittance Functions

In the present invention, the immittance functions may be selected from, for example, a complex impedance transfer function (which may be termed $Z^*$), a complex admittance function (which may be termed $Y^*$), a complex modulus transfer function (which may be termed $M^*$), a complex dielectric constant transfer function (which may be termed $\varepsilon^*$), a complex capacitance transfer function (which may be termed $C^*$), a complex conductance transfer function (which may be termed $\tau^*$), and combinations thereof.

The impedance immittance function, and its components, can be generated as described above. Other impedance functions can be determined individually, i.e. directly obtained, by experiment on the system of interest (e.g. the first system as it is termed herein) or, preferably, by determining a first immittance function and then generating one or more further immittance functions from the first immittance function. This can be carried out for a plurality of known values for the parameter of interest, e.g. the concentration of a target species in a solution. From this, the variation in the plurality of immittance functions and their components with the parameter of interest can be determined. The nature of the variation can then be compared, and the most appropriate immittance function or immittance function component selected for use in a test step where the parameter of interest is not known, but needs to be determined.

The complex admittance function can be determined for a system as follows. The mathematical inversion of impedance $Z^*(\omega)$, with its real and imaginary components, leads to the generation of another complex function known as admittance, $Y^*(\omega)$. This function can be directly obtained if the applied perturbation is $I(t)=\bar{I}+\tilde{I}e^{(j\omega t)}$ with a response $V(t)=\bar{V}+\tilde{V}e^{(j\omega t-\phi)}$ so that $$Y^*(\omega) = \frac{\tilde{I}}{\tilde{V}} \frac{e^{j\omega t}}{e^{(j\omega t-\phi)}} = |Y|e^{j\phi}$$

wherein $I(t)$ is the applied current having a steady state value $\bar{I}$, and a varying overlaid current with an magnitude $\tilde{I}$ and frequency $\omega$, and $V(t)$ is the response potential, having a steady state value $\bar{V}$, magnitude of varying potential $V$ and frequency $\omega$, and $\phi$ is the phase shift.

In an embodiment, the method may involve determining a first immittance function for a first system and then generating one or more second immittance functions from the first immittance function for the first system, for example using a phasorial analysis, and then determining or comparing how the first and one or more second immittance functions vary with the parameter of interest. The determining of a first immittance function for a system can be obtained from analysis of the applied varying potential or current, and the subsequent analysis of the relationship between the applied varying potential or current and the resultant varying current or potential, respectively, which can be carried out using any conventional equipment or hardware, such as an electrical impedance spectrometer, and then Frequency Response Analysis (FRA) can then be used to generate the first immittance function. From this first immittance function, the one or more second immittance functions can be generated using a computer program that carries out a mathematical phasorial analysis, e.g. using the relationships shown in Table I below, on the first immittance function.

In an embodiment, the method may involve determining a first immittance function for a first system and then generating one or more second immittance functions from the first immittance function for the first system, for example using a phasorial analysis, deriving at least one component for the first admittance function and at least one component for each of the one or more second immittance functions, and then determining or comparing how the at least one component for the first admittance function and the at least one component for each of the one or more second immittance functions vary with the parameter of interest, and, optionally, selecting a component for use in an electrochemical test. The electrochemical test may be an electrochemical assay, for example an assay to determine the concentration of a species in a carrier medium.

In an embodiment, the method may involve determining a first immittance function for a first system, which is an impedance immittance function, and then generating one or more second immittance functions for the first system other than an impedance function from the first immittance function, for example using a phasorial analysis, and then determining how the first and one or more second immittance functions and/or the components thereof vary with the parameter of interest, and, optionally, selecting a component for use in an electrochemical test.

In an embodiment, the method may involve determining a first immittance function for a first system, which is a complex impedance ($Z^*$) transfer function, and then generating one or more second immittance functions for the first system selected from a complex admittance function (which may be termed $Y^*$), a complex modulus transfer function (which may be termed $M^*$), a complex dielectric constant transfer function (which may be termed $\varepsilon^*$), a complex capacitance transfer function (which may be termed $C^*$), a complex conductance transfer function (which may be termed $\tau^*$), for example using a phasorial analysis, and then determining how the first and one or more second immittance functions and/or the components thereof vary with the parameter of interest, and, optionally, selecting a component for use in an electrochemical test.

The present inventors have found that they can generate, from a first immittance function, a plurality of other immittance functions using phasorial analysis. The phasorial analysis may be carried out using any suitable computational means, e.g. a computer program. The phasorial relationships between different immittance functions are given in Table I below.

If one of the functions of the immittance function table (or matrix) is obtained, any others can be easily obtained through the mathematical operations tabulated below in the "immittance matrix". For instance, $Z^*$ is a function of frequency $Z^*(s)$ during measurements. The complex function, $Z^*(s)=Z'+jZ''$, can be obtained from commercial EIS equipment that generates a table of $Z'$ and $Z''$ for each $\omega$ sampling frequency. This gives a table (or ASCII file) with three columns of data: $\omega_i \ldots \omega_f$ (first column), $Z'_i \ldots Z'_f$ (first column) and $Z''_i \ldots Z''_f$, where i is the initial frequency and f is the final frequency and i-f is the frequency range of the experiment. These columns of numbers can be readily treated mathematically, using the relationships shown in the table, to generate the other tabulated functions.

TABLE I

| | Immittance functions and their phasorial relationships | | | | | |
|---|---|---|---|---|---|---|
| | $M^*$ | $Z^*$ | $Y^*$ | $\varepsilon^*$ | $C^*$ | $\sigma^*$ |
| $M^*$ | $M^*$ | $\varphi Z^*$ | $\varphi(Y^*)^{-1}$ | $(\varepsilon^*)^{-1}$ | $C_e(C^*)^{-1}$ | $\varphi(\chi\sigma^*)^{-1}$ |
| $Z^*$ | $\varphi^{-1}M^*$ | $Z^*$ | $(Y^*)^{-1}$ | $\varphi^{-1}(\varepsilon^*)^{-1}$ | $\varphi^{-1}C_e(C^*)^{-1}$ | $\chi^{-1}(\sigma^*)^{-1}$ |
| $Y^*$ | $\varphi(M^*)^{-1}$ | $(Z^*)^{-1}$ | $Y^*$ | $\varphi\varepsilon^*$ | $\varphi C_e^{-1}C^*$ | $\chi\sigma^*$ |

TABLE I-continued

Immittance functions and their phasorial relationships

|  | M* | Z* | Y* | ε* | C* | σ* |
|---|---|---|---|---|---|---|
| ε* | $(M^*)^{-1}$ | $\varphi^{-1}(Z^*)^{-1}$ | $\varphi^{-1}Y^*$ | $\varepsilon^*$ | $C_e^{-1}C^*$ | $\varphi^{-1}x\sigma^*$ |
| C* | $C_e(M^*)^{-1}$ | $C_e\varphi^{-1}(Z^*)^{-1}$ | $C_e\varphi^{-1}Y^*$ | $C_e\varepsilon^*$ | $C^*$ | $s^{-1}x\sigma^*$ |
| σ* | $\varphi(xM^*)^{-1}$ | $(xZ^*)^{-1}$ | $x^{-1}Y^*$ | $\varphi x^{-1}\varepsilon^*$ | $sx^{-1}C^*$ | $\sigma^*$ |

$s=j\omega$ and $\phi=sC_e$ in which $C_e=\varepsilon_0 x$ and where $x=A/l$. A is the electrode effective area (determined experimentally), l is the thickness of an electrode modifying film/monolayer (determined experimentally or assumed), and $\varepsilon_0$ is the dielectric permittivity of free space, $8.854\times10^{-12}$ F/m. x is thus a geometric parameter.

In the above table, Z* indicates a complex impedance transfer function, M* indicates a modulus transfer function, ε* indicates a complex dielectric transfer function, C* indicates a complex capacitance transfer function, τ* indicates a complex conductance transfer function.

Each of the entries in the table above indicates how a given first immittance function (shown in the first row heading) must be treated to obtain another immittance function (shown in the first column headings). Table I above, for example, shows the phasorial (defined here as $s=j\omega$, where $j=\sqrt{-1}$) or complex inversion (for instance, $Z^*=(Y^*)^{-1}$) interchange between different immittance functions.

The present inventors have found that although the immittance functions shown in Table I are mathematically related, changes in the analysed current signal (or potential signal) as induced by an interfacial event at a working electrode surface, could affect some dramatically and others minimally (as demonstrated in the Examples). For instance, the complex capacitance function, has a totally different meaning and potentially different arena of sensing to the (simultaneously acquired) complex impedance function. The access of one or the other physical aspect of the system the depends on the phase shift and modulus. In other words, all functions and related physical meanings can be derived from the analysis of phase shift and modulus of the voltage/output current.

Generally, as indicated above for each immittance function, there will be a sub-set of components that can be determined, i.e. imaginary and real parts, modulus and an associated phase. For instance, the complex capacitance immittance function C* can be resolved into its imaginary component C", its real component C', the modulus |C| and the associated phase φ.

The present inventors have found that typically there is one immittance function or immittance function component that is more sensitive than the others to a change in a parameter of interest over a certain range. It may be that over a certain range for a parameter of interest one particular immittance function or component thereof is most sensitive, but for other ranges, other immittance functions or components thereof are more sensitive. If the surface of the working electrode applying the varying potential or current is biosensory, e.g. having one or more probe molecules specific for a target molecule (sometimes termed an analyte), a plurality of immittance functions can be generated as a function of its exposure to the target molecule at different concentrations. The variation of the different immittance functions and their components over the different concentrations can be compared, and the immittance function that is most appropriate, e.g. most sensitive or has highest correlation with the variation in the concentration, can be selected. The generation of immittance functions, their components and their comparison with the parameter of interest, and the selection of the most appropriate immittance function may be carried out automatically, for example on a device including software that can carry out the method.

The present inventors have found that considerably more information about the interface at a working electrode (which may, for example, be a sensory interface) can be obtained than standard forms of impedance analysis.

The present inventors have found that the measurement of modulated current or potential as a function of a varying voltage or current, respectively, can be used to generate an entire library of immittance functions for a system of interest (e.g. the first system as termed herein), each with a subset of components; the physical interpretation of these and their response to changes (e.g. recognition events) at any given electrode will be demonstrated in the Examples below. The present inventors have found that the method is suitable for automation, such that a device can carry out, for a system of interest (e.g. the first system described herein) the determining of the immittance functions and/or components thereof, comparison of the immittance functions and/or components thereof with the variation of a parameter of interest, and selection of the most appropriate immittance function or immittance function component to use in a subsequent electrochemical test in which the parameter of interest is unknown in a second system. The first system typically provides a suitable calibration system for the second system.

The method may involve
(i) determining a plurality of immittance functions for a first system, and determining or comparing how a plurality of immittance functions and/or components thereof vary with a change in a parameter of interest for the first system, and then selecting an immittance function or component thereof for use in an electrochemical test;
(ii) carrying out an electrochemical test step for a second system to determine at least one value for the immittance function or component thereof selected in step (i), and then, by using a quantitative relationship between the selected immittance function and the certain parameter, determining a value in the parameter of interest.

The method may involve determining a plurality of immittance functions for a first system, deriving at least one component for each immittance function and comparing how the at least one component for each immittance function varies with a change in a parameter of interest for the first system, and then selecting a component of one of the immittance functions, which can then be used in an electrochemical test.

In an embodiment, the method may involve comparing how a plurality of immittance functions and/or components thereof vary with a change in a parameter of interest for a first system, and then selecting an immittance function or component thereof for use in an electrochemical test.

In an embodiment, the method may involve determining a first immittance function for a first system, which is an impedance immittance function, determining one or more second immittance functions other than an impedance immittance function for the first system, and then determining how the first and one or more second immittance functions and/or the components thereof vary with the parameter of interest, and, optionally, selecting a immittance function or a component thereof for use in an electrochemical test.

Preferably, the determining of the plurality of immittance functions is carried out at plurality of applied frequencies of potential or current, and the comparing of the immittance functions and/or components thereof with the parameter of interest is carried out at each of the applied frequencies, and the method then involves selecting a frequency to use, together with the an immittance function or immittance function component, in the subsequent electrochemical test according to predetermined criteria. For example, the frequency and an immittance function or immittance function component may be selected such that together they provide the greatest variation in the immittance function and/or component(s) thereof with the parameter of interest and/or greatest correlation in the variation of the immittance function and/or component(s) thereof with the parameter of interest.

In an embodiment, the comparing involves (i) determining or comparing the extent of variation of the immittance functions and/or components thereof with the change in the parameter of interest and/or (ii) determining or comparing the correlation of the variation of the immittance functions and/or functions with the change in the parameter of interest.

In an embodiment, the determining involves plotting a component of each immittance function against either the concentration of a species in a carrier medium in the first system or the logarithm of the concentration of a species in a carrier medium in the first system.

In an embodiment, the selecting of the immittance function or component thereof for use in an electrochemical test is selected from (i) selecting an immittance function having the highest variation with the amount of change in the parameter of interest; (ii) selecting an immittance function having the highest correlation with the parameter of interest; (iii) selecting an immittance function with a variation with the amount of change in the parameter of interest above a preselected threshold and/or (iv) selecting an immittance function having a correlation with the parameter of interest above a preselected threshold; or a combination thereof.

In an embodiment, the method involves, applying an alternating potential or alternating current to a first system over a plurality of values for a parameter of interest and monitoring, respectively, the response in terms of, respectively, the output alternating current or output alternating potential, and using a relationship between the applied alternating potential or alternating current and, respectively, the output alternating current or output alternating potential, calculating a plurality of immittance functions and/or components thereof for each of the values of the parameter of interest.

The frequency of the alternating potential and/or alternating voltage may be in the range of 1 mHz to 1 MHz.

The electrochemical test method may be a computer implemented method, wherein the method is carried out using a computer, which may control apparatus for carrying out electrochemical tests, e.g. an electrochemical impedance spectrometer, and which may automatically carry out the determining, the comparing and selecting steps, as described herein.

Preferably, in the determining and/or comparing, the method does not use an assumed equivalent circuit. Preferably the method is a label-free method for detecting a target species.

In an aspect, the present invention provides a computer program for carrying out and/or controlling apparatus for carrying out the method.

In aspect, the present invention provides a computer program, wherein the program carries out a method comprising:

comparing how a plurality of immittance functions and/or components thereof vary with a change in a parameter of interest for a first system, and then selecting an immittance function. The comparing may be as described herein. The comparing may involve (i) comparing the extent of variation of the immittance functions and/or components thereof with the change in the parameter of interest and/or (ii) comparing the correlation of the variation of the immittance functions and/or functions with the parameter of interest. The selecting of the immittance function or component thereof for use in an electrochemical test may be selected from predetermined criteria, for example criteria selected from (i) selecting an immittance function having the highest variation with the amount of change in the parameter of interest; (ii) selecting an immittance function having the highest correlation with the parameter of interest; (iii) selecting an immittance function with a variation above a preselected threshold with the amount of change in the parameter of interest and/or (iv) selecting an immittance function having a correlation with the parameter of interest above a preselected threshold.

Optionally, before the comparing, the program generates, from a first immittance function for a first system, one or more second immittance functions for the first system, and then determines how the first and one or more second immittance functions and/or components thereof vary with the parameter of interest. The may be carried out as described above, for example with reference to the relationships between the immittance functions given in Table I above. The first immittance function may be a complex impedance immittance function, and the second immittance function selected from a complex admittance function, a complex modulus transfer function, a complex dielectric constant transfer function, a complex capacitance transfer function, a complex conductance transfer function, and combinations thereof (including, ni an embodiment, combinations of their real and imaginary components).

The computer program may be further adapted to control an apparatus to carry out an electrochemical test step for a second system to determine at least one value for the immittance function or component thereof selected following the comparing step, and then, by using a quantitative relationship between the selected immittance function and the parameter of interest, determining a value in the parameter of interest. The apparatus may be as described herein.

The computer program may be stored/distributed on a suitable medium, such as an optical storage medium or a solid-state medium supplied together with or as part of other hardware, but may also be distributed in other forms, such as via the Internet or other wired or wireless telecommunication systems.

Figure 13:
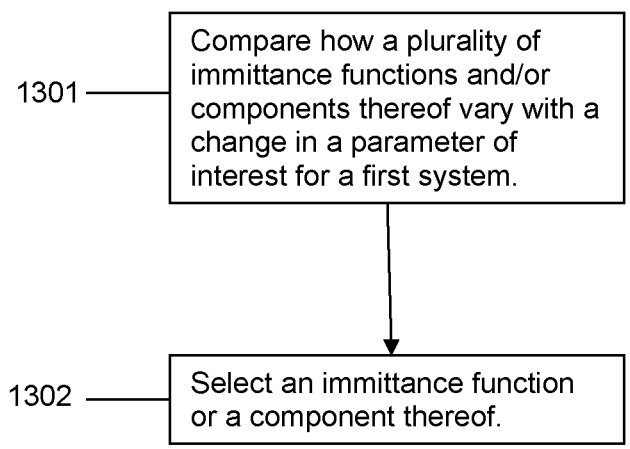
FIG. 13 illustrates schematically an embodiment of a computer program described herein.

An embodiment of a computer program is illustrated schematically in FIG. 13, wherein, in step 1301, the program compares how a plurality of immittance functions and/or components thereof vary with a change in a parameter of interest for a first system. In subsequent step, 1302, the program selects an immittance function or a component thereof.

Figure 14:
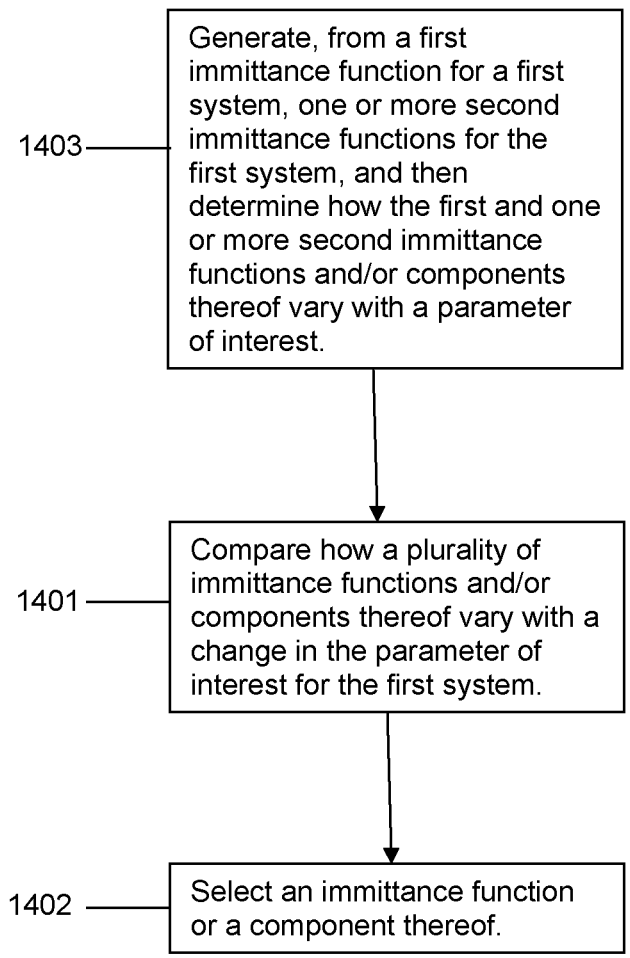
FIG. 14 illustrates schematically a further embodiment of a computer program described herein.

A further embodiment of a computer program is illustrated schematically in FIG. 14, wherein, in step 1401, the program compares how a plurality of immittance functions and/or components thereof vary with a change in a parameter of interest for a first system. In subsequent step, 1402, the program selects an immittance function or a component thereof. In this embodiment, the program includes a step 1403, before step 1401, that generates, from a first immittance function for a first system, one or more second immittance functions for the first system, and then determines how the first and one or more second immittance functions and/or components thereof vary with a parameter of interest.

The invention further provides an apparatus for use in an electrochemical test method, wherein the apparatus is adapted to carrying out the electrochemical method as described herein and/or adapted to run a computer programme as described herein. The apparatus may comprise an electrochemical impedance spectrometer. In an embodiment, the apparatus comprises an electrochemical impedance spectrometer that is capable of measuring at least one immittance function, preferably a complex impedance function. The apparatus preferably is adapted to (i) compare how a plurality of immittance functions and/or components thereof vary with a change in a parameter of interest for a first system, and then select an immittance function or component thereof for use in an electrochemical test; and (ii) carry out an electrochemical test step for a second system to determine at least one value for the immittance function of component thereof selected in step (i), and then, by using a quantitative relationship between the selected immittance function and the parameter of interest, determining a value in the parameter of interest. The comparing and selecting in step (i) may be carried out automatically by the apparatus. The apparatus may be adapted to carrying out of the electrochemical test step for the second system automatically. The apparatus may be further adapted to carry out a step, before the comparing step (i), of determining for the first system how the plurality of immittance functions and/or components thereof vary with a change in a parameter of interest and determining the quantitative relationship between the selected immittance function and the parameter of interest. The apparatus may be adapted to carry out a step, before the comparing step (i), of determining a first immittance function for a first system and then generating one or more second immittance functions from the first immittance function for the first system, for example using a phasorial analysis, and then determining how the first and one or more second immittance functions vary with the parameter of interest. In an embodiment, the first immittance function is a complex impedance function, and the one or more second immittance functions are selected from a complex admittance function, a complex modulus transfer function, a complex dielectric constant transfer function, a complex capacitance transfer function, a complex conductance transfer function, and combinations thereof (including combinations of their real and imaginary components).

The determining may be a involve direct measurement of electrochemical data of the first system to obtain an immittance function, e.g. the first immittance function.

If the apparatus comprises an electrochemical impedance spectrometer, the electrochemical impedance spectrometer may be of a standard design. The electrochemical impedance spectrometer may comprise a working electrode, a counter electrode, and, if desired, a reference electrode. The electrochemical impedance spectrometer preferably comprises a means for applying, controlling and varying a potential between the working and counter electrodes, and a means for measuring the resultant current. The electrochemical impedance spectrometer preferably comprises a potentiostat for controlling the potential and measuring the resultant current. The electrochemical impedance spectrometer preferably comprises a means for calculating impedance data from the potential applied and the resultant current. The electrochemical impedance spectrometer may comprise a means for calculating electron transfer resistance of the working electrode.

Screening and Optimizing Immittance Functions for a Specific Application

As described above, the present inventors have found the method of the present invention can be automated on a device, so that the most appropriate immittance function or immittance function component for a variation in a parameter of interest is automatically selected for a system of interest, e.g. the first system as described herein, and then this immittance function used in a second system to determine a value for the parameter of interest from a measured value of the selected immittance function or immittance function component. The method is widely applicable and may be used on an individual or Multiplexed Frequency Response Platform (MFRP) to monitor any LTI (Linear Time-invariant) sensing or responsive surface. The plurality of immittance functions discussed above can be generated from any given initial current-voltage data set for a system of interest automatically. For these functions, the imaginary, real, modulus and phase can be recorded. This can all proceed, in a manner analogous to the plug-and-play concept in computing, without user intervention (and with no prior assumptions about the surface or the working electrode or optimal function or equivalent circuit). Preferably, for a device carrying out the method for a given system and variation of a parameter of interest, software will generate and/or compare a library of (i.e. a plurality of) immittance functions, and will automatically calibrate the device to the immittance function which is selected according to predetermined criteria, e.g. the most sensitivity to the variation in the parameter of interest and/or the highest correlation with the variation in the parameter of interest.

Once the most appropriate immittance function, immittance function component or combination of such components has been selected in the method for a system, the frequency of analysis will be optimized and subsequent data acquisition accordingly will be much faster (since only specific data acquired at the optimal frequency will be gathered) i.e. the need to a full frequency range of data is only necessary on the first screening for calibration and immittance function analysis. The present inventors consider the method and related aspects described herein to be unique and to represent an improvement on current electroanalytical procedures. The present inventors consider the method can be used in disease marker detection, where receptive aptamers or antibodies, for example, are immobilized through different chemical means on a working electrode and used to detecting targets of markedly variable chemical and physical composition. Subsequent interfacial changes at the working electrode may be capacitive, impedance, current, phase, charge transfer resistance or indeed of any other immittance function (or component or combination thereof). Typically, in prior art methods, e.g. standard electrochemical impedance spectroscopy, only one of these parameters has been assayed, often at one frequency only and by users requiring good electrochemical knowledge. In many cases this approach fails or is limited only one specific surface formulation/target. It is been known that the most sensitive parameter is highly reflective of the surface chemistry and recognition chemistry employed at the chip surface and, thus, a single approach is unlikely to be effective in many situations, or to at least be unlikely to be optimized, particularly if one seeks to detect several markers simultaneously in a multiplexed format (using arrays of electrodes functionalised in a different way with different receptors).

The present inventors consider that the present method and related aspects have considerable and powerful application across many areas. The method may, for example, be used in the label free detection of biological target molecules (immunoassays) and in fundamental bioelectrochemistry (and thus potentially enzyme based biosensing).

The term system, in the present application, indicates a physical environment around a working electrode used to obtain the electrochemical data to generate the immittance functions. In a preferred embodiment, the first system provides a suitable system for calibrating the parameter of interest for a second system. For example, the first and second systems may have one or more commonalities selected from, but not limited to, electrodes of the same or substantially the same type, probe moieties immobilised on the electrodes, wherein the probe moieties and/or electrodes are of substantially the same or same type, target species of substantially the same type or same type, which optionally may be in a carrier medium of substantially the same or the same type. In an embodiment, all or substantially all aspects of the first and second systems are the same except for the possible difference in the parameter of interest, e.g. concentration of a target species, for the first and second systems.

In an embodiment, the first and/or second system comprises a carrier medium comprising a target species, and a working electrode in contact with the carrier medium, and, optionally, the parameter of interest is the concentration of the target species in the carrier medium. The working electrode may have on a surface thereof probe moieties that bind to the target species.

The carrier medium may be in gaseous form, liquid form or solid form.

The carrier medium may be in liquid form, and the target species may be suspended and/or dissolved in the carrier medium. The target species may be selected from, but is not limited to, proteins, polypeptides, antibodies, nanoparticles, drugs, toxins, harmful gases, hazardous chemicals, explosives, viral particles, cells, multi-cellular organisms, cytokines and chemokines, ganietocyte, organelles, lipids, nucleic acid sequences, oligosaccharides, chemical intermediates of metabolic pathways and macromolecules. In preferred embodiments, the target species comprises, consists essentially of, or consists of, a biological molecule, more suitably a biological macromolecule, most suitably a polypeptide.

If the target species is a protein, the protein may be selected from, but is not limited to, native proteins, denatured proteins, protein fragments, and prokaryotically or eukaryotically expressed proteins. Protein may have its normal meaning in the art, and most preferably 'protein' refers to a polypeptide molecule. Such polypeptide may comprise modifications such as glycosylation; phosphorylation or other such modifications.

If the target species is an antibody, the antibody may be selected from one or more of the classes IgA, IgD, IgE, IgG and IgM.

If the target species is a nanoparticle, the nanoparticle can be selected from, but is not limited to, one or more of insulating, metallic or semiconducting nanoparticles.

If the target species is a drug, the drug may be selected from, but is not limited to, alcohol (e.g. ethanol), amphetamines, amyl nitrate, heroin, ketamine, anabolic steroids, LSD, solvents, cannabis, cocaine (such as cocaine hydrochloride or 'coke'), tobacco, tranquilisers, crack (i.e. cocaine free base), ecstasy and/or gammhydroxybutyrate (GHB). Alternatively, in some embodiments, the drug may be a medicinal substance.

The target species may be a candidate drug, e.g. a chemical or biological entity which may be tested or screened for a particular activity or property using the present invention.

If the target species is a toxin, the toxin may be selected from, but is not limited to, one or more toxins originating from animals, plants, or bacteria.

If the target species is a viral particle, the viral particle may be selected from, but is not limited to, one or more viral particles with and without a genome.

If the target species is a cell, the cell may be selected from, but is not limited to, one or more of pluripotent progenitor cells, human cells (e.g. B-cells, T-cells, mast cells, phagocytes, neutrophils, eosinophils, macrophages, endothelial cells), cancerous cells (e.g. those originating from liver, cervical bone, pancreatic, colorectal, prostate, epidermal, brain, breast, lung, testicular, renal, bladder cancers), unicellular organisms of non-human origin, algae, fungi, bacteria, plant cells, parasite eggs, plasmodia and mycoplasma.

If the target species is an organelle, the organelle may be selected from, but is not limited to, one or more of nucleus, mitochondria, Golgi apparatus, endoplasmic reticulum, lysosome, phagosome, intracellular membranes, extracellular membranes, cytoskeleton, nuclear membrane, chromatin, nuclear matrix and chloroplasts.

If the target species is a lipid, the lipid may be selected from, but is not limited to, one or more of signalling lipids, structural lipids, phospholipids, glycolipids and fatty acids.

If the target species is nucleic acid sequence, the nucleic acid sequence may be selected from, but is not limited to, one or more of DNA, cDNA, RNA, rRNA, mRNA, miRNA and tRNA.

If the target species is an oligosaccharide, the oligosaccharide may be selected from, but is not limited to, one or more of oligosaccharides of human, animal, plant, fungal or bacterial origin.

In a preferred embodiment, the target species is a protein. The method and other aspects of the invention may be used for the detection or identification of a proteins.

The target species may be any antigen or analyte that is indicative of a particular disease. The target may be selected from, for example, angiotensin I converting enzyme (peptidyl-dipeptidase A) 1; adiponectin; advanced glycosylation end product-specific receptor; alpha-2-HS-glycoprotein; angiogenin, ribonuclease, RNase A family, 5; apolipoprotein A-I; apolipoprotein B (including Ag(x) antigen); apolipoprotein E; BCL2-associated X protein; B-cell CLL/lymphoma 2; complement C3; chemokine (C—C motif) ligand 2; CD 14, soluble; CD 40, soluble; cdk5; C-reactive protein, pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alpha-melanocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, clade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor and the like. Markers useful for diabetes include for example C-reactive protein, glucose; insulin; TRIG; GPT; HSPA1 B; IGFBP2; LEP; ADIPOQ; CCL2; ENG; HP; IL2RA; SCp; SHBG; and TIMP2.

The target may be a target associated with monitoring diabetes. In an embodiment, the target may be selected from glucose, insulin, Interleukin 2 receptor alpha (IL2-RA), C-reactive protein (CRP) and glycated hemoglobin (HbAlc). If the target is glucose, the probe moieties may be selected from, for example, the molecular recognition element of GDH-FAD assay or a glucose/galactose binding protein ("GGBP") (Scholle, et al., Mol. Gen. Genet 208:247-253 (1987)). If the target is IL-2RA, the probe moieties may comprise or consist of a monoclonal antibody specific for IL-2RA.

The carrier medium may comprise a biological fluid sample, e.g. collected from a human or animal subject. The target species, which may be in the biological fluid sample, may be selected from metabolic products such as glucose, lactate, uric acid, ascorbic acid, catecholamines such as norepinephrine, epinephrine, and dopamine, $O_2$, ions such as sodium and calcium, whole human cells, pathogens including bacteria, fungi, parasites, and viral particles, metal ions such as zinc, and protein biomarkers such as inflammatory cytokines.

The probe moieties may be selected from, but are not limited to, one or more of a biological macromolecule, an aptamer, a peptide aptamer, a recognition reagent presented in the context of another engineered protein scaffold, a DNA aptamer, a RNA aptamer, a chemical entity, a chemical entity of potential therapeutic value, a oligosaccharide, a peptide, a protein and an antibody. Preferably, the probe moieties are selected from one or more of an antibody, a nucleic acid and a peptide. Preferably, the probe moieties bind selectively to the target species.

If the probe moieties comprise an antibody, the antibody may be selected from one or more of the classes IgA, IgD, IgE, IgG and. IgM. The antibody preferably binds selectively to the target species.

In an embodiment, the first and/or second systems comprise a working electrode having the probe moieties immobilised thereon. In an embodiment, the first and/or second system comprise a plurality of electrodes having the probe moieties immobilised thereon. Each of the first and/or second systems may comprise a plurality of electrodes, and the plurality of electrodes may be in an array. Each of the plurality of electrodes is preferably individually addressable.

"Individually addressable" is a term known in the art and means that each electrode of the array or electrode structure can be connected electrically to external devices on its own, i.e. without the need for connecting other electrodes of the array at the same time. In an embodiment, the array may be capable of detecting a plurality of target species. For example, the array be comprise a plurality of electrodes, each of which has probe molecules thereon, wherein the probe molecules on at least two of the plurality of electrodes are capable of binding to different target species to one another.

Each of the first and/or second systems may comprise a plurality of electrodes in an array. Preferably, the array comprises at least 10, more preferably at least 20, more preferably at least 50, more preferably at least 100, more preferably at least 1,000, more preferably at least 10,000 electrodes, each of which may be individually addressable.

Optionally, in the first system, a plurality of working electrodes are present, each in contact with a carrier medium containing a target species at a known concentration, with the carrier medium being the same for each working electrode, but the concentration of the target species in each carrier medium being different for each working electrode and the immittance functions and/or components thereof are determined for each electrode at a preselected frequency of applied potential or current. This allows for the comparison of the variation of the immittance functions and/or components thereof with a variation in the concentration of the target species. This may be carried out for a plurality of frequencies for the applied potential or current to allow for comparison of variation of the immittance functions and/or components thereof with the variation in the concentration of the target species.

The method and other aspects of the invention are applicable to electrodes of any scale. In some embodiments, it is particularly beneficial to arrays of small electrodes. In some embodiments, the first and/or second systems comprise electrodes having a diameter (largest dimension) of not more than 50 µm, more preferably not more than 20 µm, more preferably not more than 1 µm, more preferably not more than 500 nm, more preferably not more than 200 mn, more preferably not more than 50 nm. Diameter in the present context can indicate the largest dimension, since the electrodes may not always assume geometrically recognised shapes due to manufacturing tolerances or other considerations. Thus, for asymmetric or finger-shaped or other forms of electrodes, 'diameter' can be interpreted accordingly to mean 'width' or 'largest dimension', suitably the largest dimension parallel with the plane of the substrate on which the electrode is located.

The methods of the present invention may be applied to electrode structures or electrode array structures where the electrodes are closely spaced, in particular, the minimum distance (separation) between the electrodes is preferably less than 100 µm, preferably below 50 µm, more preferably below 20 µm, more preferably below 1 µm, more preferably below 200 run and most preferably below 50 nm.

The method may be applied to electrode structures or electrode array structures with a high densities of electrodes, including, but not limited to, electrode structures or electrode array structures with electrode-densities of preferably $10/cm^2$ or more, more preferably of $100/cm^2$ or more, more preferably of than $1000/cm^2$ or more, more preferably of more than $10000/cm^2$.

The electrodes used in the method herein, e.g. in the first and/or second system, are formed of electrically conductive material. Preferably these materials are metallic but can for instance be non-metallic such as carbon or semiconductor materials. Gold, silver, platinum, copper or aluminium, and, in particular gold, are preferred.

The first and second system will typically comprise a counter electrode, as well as the working electrode, which may be of the same or a different type of material as the counter electrode. A reference electrode may also be present in the first and/or second systems. The potential applied to, and the current monitored between, the working and counter electrodes may be applied and controlled by a potentiostat, as would be understood by the skilled person.

Aspects of the present invention will now be described with reference to the following non-limiting Examples and the accompanying Figures.

EXAMPLES

Example 1—Immunoassay Applications: Biofunctionalized Transducer Surfaces and Label Free Detection of Disease Markers Traditional Impedance Spectroscopy Approach Versus Immittance Function Approach As mentioned above, the sensitive detection of clinically important target molecules can be achieved through the immobilization of appropriate receptors on an electrode surface and the subsequent mapping out of electronic or electrochemical characteristics of this interface as a function of target binding. The present inventors show here not only that some immittance functions can be very sensitive and calibratable probes of a target but also that the best function to track depends very much on the receptive interface constructed and the target.

Interfaces receptive to specific (e.g. clinically important) targets can be generated by laying down combinations of surface chemistries and biological receptors (most often antibodies or aptamers). In an EIS analysis the impedance characteristics of such interfaces are then screened as a function of target concentration in generating analytical curves. The present inventors start here by showing that the standard means of assessing such data (that is through the use of an equivalent circuit) is not only unnecessary and inherently limiting, but also inferior even when the immittance function being sampled is the real part of the fundamental function $Z^*$.

All chemicals were purchased from Sigma-Aldrich unless stated. HS—$C_{11}H_{22}$-(EG)$_3$-OCH$_2$—COOH was purchased from Prochimia Surfaces, Poland. CRP was purchased from MP Biomedicals. Anti-CRP (monoclonal, goat) was from AbDSerotec. Freshly cleaned (mechanically and electrochemically) Au electrodes were immersed in a solution of 2.5 mM thiol (HS—$C_{11}H_{22}$-(EG)$_3$-OCH$_2$—COOH) in 200 µl ethanol and left to functionalise for 16 h. The electrode was then washed in pure ethanol, then deionised water, and dried under nitrogen. Antibody immobilisation was achieved through standard EDC/NHS bioconjugation chemistry; a solution of 0.4 M EDC and 0.1 M NHS was prepared and added to the electrode activating the terminal carboxyl groups on the thiol for 30 min. The surface was then immersed in 10 µM of the antibody in 10 mM PBS, pH 7.4 and left for 1 h. Finally the remaining NHS esters were deactivated by a 1 M ethanolamine solution for 5 min and the surface thoroughly rinsed in deionised water (18.2 M Ohm).

An Autolab model PGSTAT12 potentiostat with a FRA2 impedance module, controlled by GPES and FRA programs, was used for electrochemical measurements. A three electrode setup was used for all measurements, consisting of a 1.6 mm diameter gold working electrode (area 0.02 cm$^{-2}$), a platinum mesh counter electrode and an Ag/AgCl/3 M KCl reference electrode. EIS and CV (cyclic voltammetry) measurements were recorded in a electrolyte made of 1 mM [Fe(CN)$_6$]$^{3-/4-}$ with a supporting electrolyte of PBS, pH 7.4. CV was performed at a scan rate of 100 mV s$^{-1}$ between −0.1V and 0.5V relative to Ag/AgCl. EIS measurements were conducted in a frequency range of 50 mHz to 10 kHz in a solution of PBS containing 1 mM [Fe(CN)$_6$]$^{3-/4-}$ at fixed potential 0.25 V, the formal reduction potential of the probe relative to the reference electrode used, determined by CV on the blank electrode. All measurements were performed in triplicate.

Generated complex impedance data ($Z^*$) were processed to obtain the imaginary part of the capacitance according to $Z^*=1/j\omega C^*$, $C''=\varphi Z'$ and $C'=\varphi Z''$, where $\varphi=(\omega|Z|^2)^{-1}$ and $|Z|$ is the modulus of $Z^*$. The capacitance spectra were used to determine the influence of monolayer parameters on charge transfer resistance, i.e. the influence of capacitive contribution of the SAM to the charge transfer process. In representing the complex impedance and capacitance the influence of solution resistance $R_s$ was eliminated. Within subsequent impedance analysis, the interfacial capacitance of the SAM modified electrode was modelled by two series capacitances, those of the monolayer ($C_m$) and of the double-layer ($C_{dl}$) where $C_{dl} \gg C_m$ (meaning $C_m$ dominates in analyses). The monolayer is, additionally, configured with an associated polarization term composed of $R_t$ and $C_t$ contributions (in the Debye or Cole-Cole formulism). This charging process and its associated timescale is directly resolved in the frequency domain regime of complex capacitance and its consideration within the equivalent circuit model used FIG. 5 provides a more accurate analysis of the interface.

Figure 3:
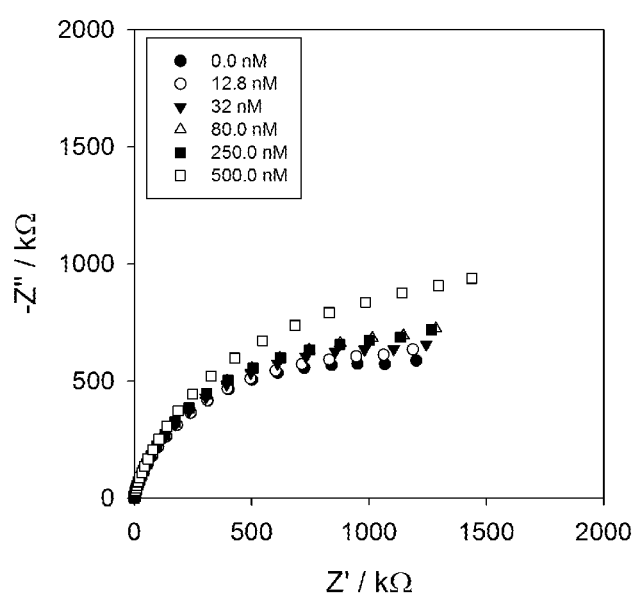
FIG. 3 shows overlaid Nyquist data plots for a prepared anti-CRP antibody interface at different concentrations of CRP target.

Between each measurement the electrode was regenerated with 1 M glycine/HCl solution at pH 2.5 or 6 mM NaOH in H$_2$O with 0.6% EtOH to remove all non-covalent interactions, and washed with PBS. BSA was used as a negative control to ensure the interface was not receptive to non-specific proteins. FIG. 3 shows overlaid Nyquist data plots for a prepared anti-CRP antibody interface at different concentrations of CRP target. The plot shows that the complex impedance, $Z^*$, responds to the target across a range of concentrations and frequencies. All the values shown here are mean values acquired from measurements across of three different electrodes. In particular, FIG. 3 shows the response of a receptive interface to the binding of a clinically important target, C Reactive Protein (CRP). It is evident, as expected, that target binding is associated with an increase in impedance. The degree to which the Z' or Z" components change is dependent on the experimental sampling frequency.

Figure 4A:
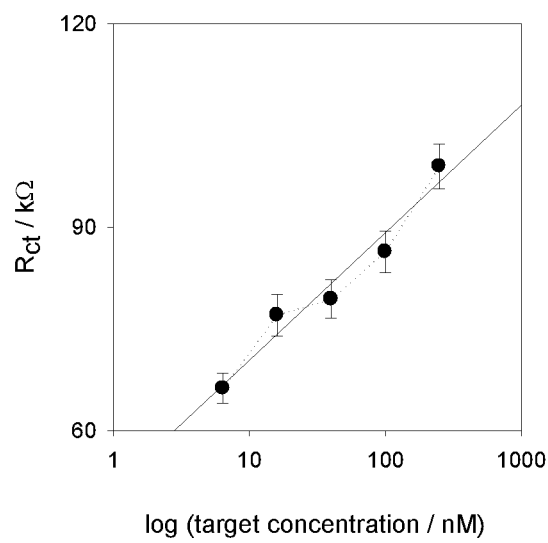
FIG. 4A. (Left) shows $R_{ct}$ plotted against concentration of target on a logarithmic scale for the interface I (values obtained from a fitting of mean values gained from three independent impedance data sets; the error bars represent errors associated with fits of impedance to an equivalent circuit model).
Figure 4B:
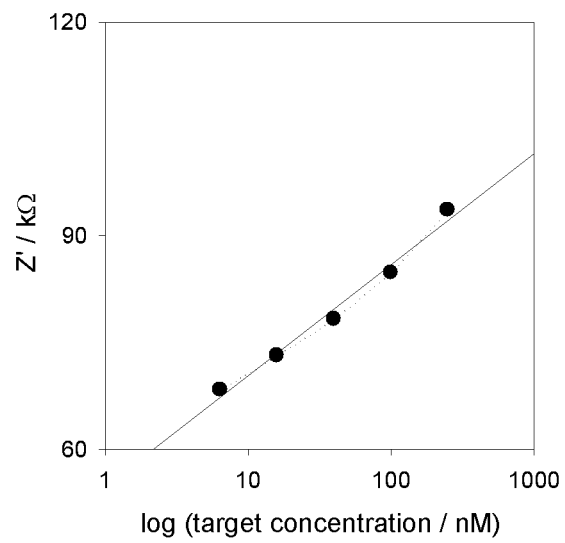
FIG. 4B (Right) shows the variance of the real part of impedance with log target concentration; data obtained at a sampling frequency of 1 Hz, where $R_{ct}$ and Z' are most correlated.

FIG. 4A (Left) shows charge transfer resistance $R_{ct}$ plotted against concentration of target on a logarithmic scale for the interface I (values obtained from a fitting of mean values gained from three independent impedance data sets; the error bars represent errors associated with fits of impedance to an equivalent circuit model). FIG. 4B (Right) shows the variance of the real part of impedance with log target concentration; (data obtained at a sampling frequency of 1 Hz, where $R_{ct}$ and Z' are most correlated). Both parameters are able to provide a good dependence as a function of target concentration but Z' is obtained with 10% less error and without need of fitting procedure. The linear dependence of the Pearson coefficient is >96% in both cases, and 98% for the real part of the impedance at this frequency. Variations of the functions are ~25% across 250 nM CRP target range.

The application of a standard "Randles" equivalent circuit fitting to sampled Z* enables the resolution of charge transfer resistance $R_{ct}$ as a function of target CRP presence, as shown in FIG. 4A. Though it is evident that $R_{ct}$ shows an adequate response to the target and can be used in the generation of an analytical curve, its linear fitting is associated with significant (~10%) error. Significantly, an equivalent analytical curve can be generated, from the same raw data, from any of the immittance functions. In FIG. 4B (right) an analytical curve is presented with Z' (obtained without any prior assumption of application of an "equivalent circuit") and notably tracks the target presence more accurately than the classically obtained $R_{ct}$ parameter.

The advantage of sampling the complex function Z* and its derived real component Z' and not resorting to the use of an equivalent circuit in these assays is again shown in a CRP binding assay with a different receptive surface in FIG. 5 where, again, the fitting of $R_{ct}$, derived from the application of a presumed equivalent circuit has associated greater fitting error.

Figure 5A:
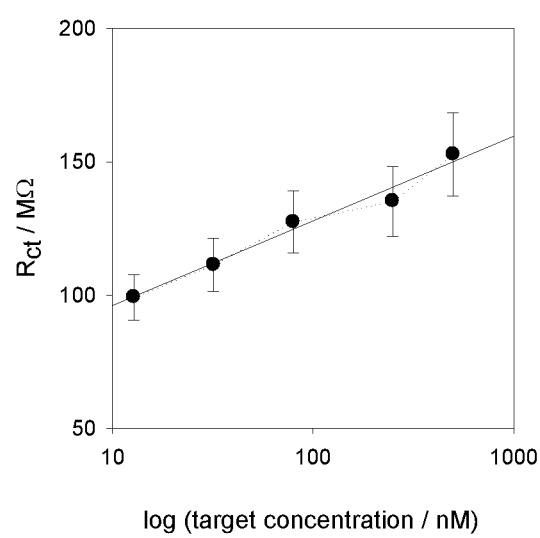
FIG. 5A. (Left) shows $R_{ct}$ plotted against concentration of target on a logarithmic scale for an alternative CRP binding interface (values obtained from a fitting of mean values gained from three independent impedance data sets; the error bars represent errors associated with fits of impedance to an equivalent circuit model).
Figure 5B:
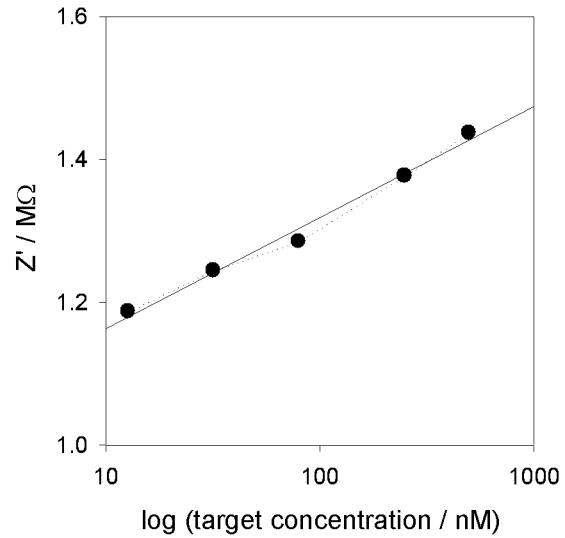
FIG. 5B (Right) shows the variance of the real part of impedance with log target concentration; data obtained at a sampling frequency of 0.1 Hz, where $R_{ct}$ and z' are most correlated.

FIG. 5A (Left) shows $R_{ct}$ plotted against concentration of target on a logarithmic scale for an alternative CRP binding interface (values obtained from a fitting of mean values gained from three independent impedance data sets; the error bars represent errors associated with fits of impedance to an equivalent circuit model). FIG. 5B (Right) shows the variance of the real part of impedance with log target concentration; data obtained at a sampling frequency of 0.1 Hz, where $R_{ct}$ and Z' are most correlated). The dependence of both parameters is equivalent to within 10%. The linear dependence of the Pearson coefficient is >96% in both cases, and 98% for the real part of the impedance at this frequency. Variations of the functions are ~50% across 250 nM CRP target range.

In extending this methodology to a broader range of immittance functions the present inventors found, for any given interface, some functions are much better reporters of specific interfacial change (such as the binding of a target molecule) than others. For the CRP receptive interface previously shown to be calibratable with the Z' function, for example, we observe that the C' function does not report on the analyte in any sensitive or calibratable manner. Because the method used a phasorial treatment of raw data with no prior assumptions about the surface or changes induced by, for example, a specific binding event, its application is independent of the specific interface used (the electrode, surface chemistry, biological chemistry etc).

FIG. 6 illustrates the variance of the real part of capacitance with CRP concentration for a receptive interface; data obtained at a sampling frequency of 1 Hz, where $R_{ct}$ and z' are most correlated as shown in FIG. 8. Variations of the functions are ~14% across a 250 nM CRP target range. Analytical curve of Y" versus logarithmic target concentration. Variations are ~45% across the same target concentration range.

On the other hand, the imaginary term of Y* complex function is observed to be highly responsive (FIG. 6).

A summary of sensitivities across a range of immittance functions is shown in Tables II and III below for two different receptive interfaces prepared for the same target (one based on an antibody, the other on a peptide aptamer), where the variation, both with function performance and with receptive film, is noteworthy.

TABLE II

Variations of the functions across 250 nM CRP target range for antibody receptive interface. C"/C' ratio function will be discussed further below.

| Immittance Function | Component | Sensitivity | Target range | Logarithmic dependence |
|---|---|---|---|---|
| Z* | Z' | ~25% | 250 nM | Yes |
| Y* | Y" | ~22% | 250 nM | Yes |
| C* | C' | ~7% | 250 nM | Yes |
| — | φ | ~3% | 250 nM | Yes |
| C* | C"/C' | ~6% | 250 nM | No |

TABLE III

Variations of the functions across 250 nM CRP target range for a non antibody receptive interface.

| Immittance Function | Component | Sensitivity | Target range | Logarithmic dependence |
|---|---|---|---|---|
| Z* | Z' | ~50% | 250 nM | Yes |
| Y* | Y" | ~45% | 250 nM | Yes |
| C* | C' | ~14% | 250 nM | Yes |
| — | φ | ~7% | 250 nM | Yes |
| C* | C"/C' | ~12% | 250 nM | No |

Finally, it has been previously suggested (Ko Ferrigno et al. US patent 2010/0234234 A1) from otherwise entirely standard EIS assays (based only on the Z* function and subsequent equivalent circuit analysis) that the phase offset between applied V and measured can serve as a good sensory function. For the receptive interfaces we are exemplifying with here, it is evident that this is not the case and, indeed that the (~7%) phase variation is greatly exceeded (in a more calibratable manner) in magnitude by the responsiveness of many of the other immittance functions one can sample.

Figure 7:
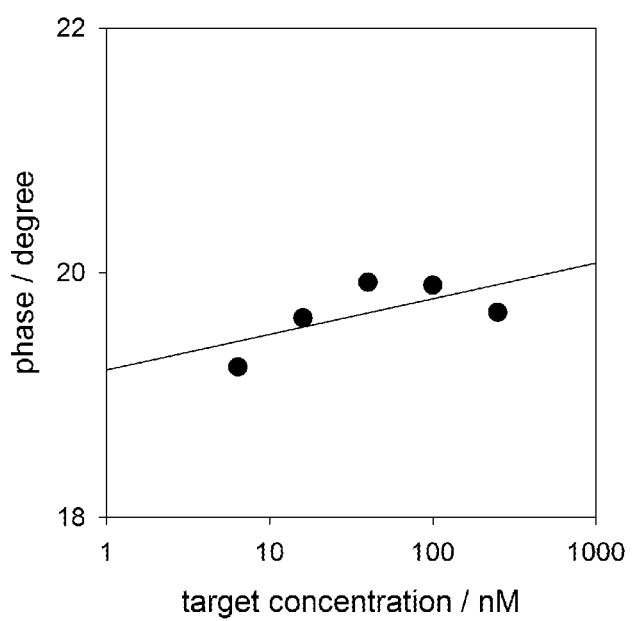
FIG. 7 shows phase changes for aptamer interface as a function of target concentration at 1 Hz.

FIG. 7 illustrates phase changes for aptamer interface as a function of target concentration at 1 Hz.

In summary, it is clear that an ability to sample a range of immittance functions is powerful in maximising the skilled person's ability to sensitively sample interfacial changes at a working electrode, where some track the desired changes sensitively and in a reproducible and calibratable manner whilst others do not and, indeed, in rolling this capability out across a very broad range of interfaces.

We could potentially add more immittance function plots here showing, with different receptors or targets, some are markedly more responsive than others.

Extending the Analytical Range

It is likely that different immittance functions will respond to target binding processes at a suitable prepared interface with different levels of sensitivity. It may be the case, for example, that one function starts to respond in a calibratable manner at exceedingly low levels or target and then saturates and becomes, thereafter unresponsive. At this point further target binding (at higher levels of target concentration) may potentially be sampled using different immittance functions. In this way the analytical range of the experiment is extended.

Because the experimental procedure is built on the application of an AC voltage trace, the frequency of voltage application forms another, highly tunable, experimental parameter. We show below that the sampling frequency has a profound effect on the degree to which functions respond.

In an embodiment, different immittance functions, components thereof, or ratios thereof are selected in step (i) of the method and used, in step (ii), for different ranges of the parameter of interest.

The Use of Ratio Functions

Any ratio of real and imaginary parts within the same or different immittance functions constitutes a function independent of the physical size or area of the assaying surface i.e. an intensive property. Significant in this is the fact that the ratio analytical function should be markedly less dependent on fabrication variables (such as those inherent in the generation of multiples of single assaying electrodes or arrays of electrodes). This may dramatically reduce batch to batch variance and coefficients of variation.

Accordingly, in an embodiment of the method, a ratio of immittance functions or components of the same or different immittance functions is selected, in step (i), for use in the electrochemical test of step (ii); and optionally the ratio is of the real and imaginary parts of the same immitance function, or components, e.g. real and imaginary parts, of different immittance functions; optionally the same or different immitance functions are selected from a complex impedance transfer function, a complex admittance function, a complex modulus transfer function, a complex dielectric constant transfer function, a complex capacitance transfer function, a complex conductance transfer function.

Automatic Frequency Optimization

Figure 8A:
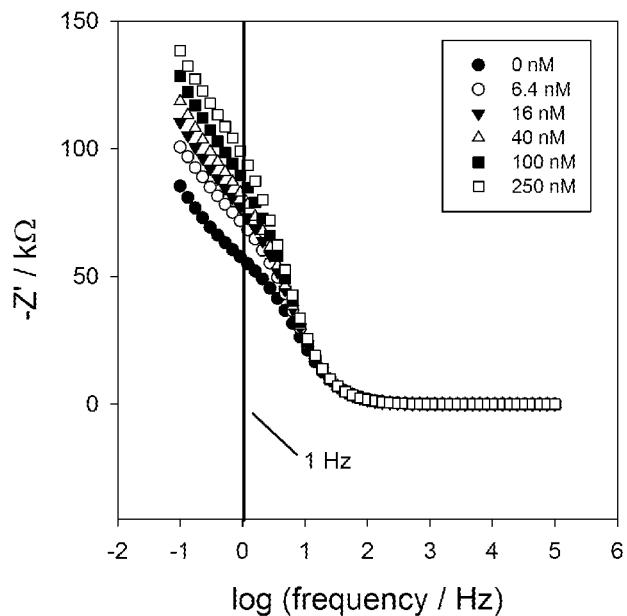
FIG. 8A shows overlaid Bode complex impedance plots of a CRP receptive interface at different concentration of target. The optimal sampling frequency (from which analytical curves can be generated) is 1 Hz here.
Figure 8B:
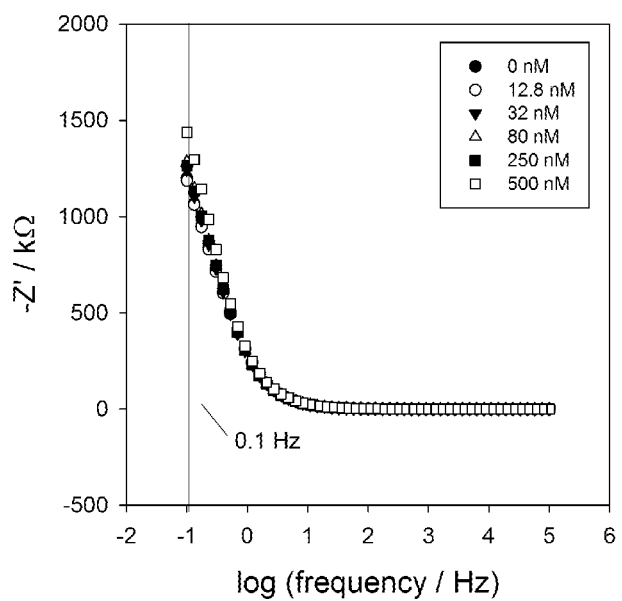
FIG. 8B shows overlaid Bode complex impedance plots for a different CRP responsive interface. Here, the optimal sampling frequency is 0.1 Hz (right).

As explained above, the response of any one immittance function to sampling frequency can be summarized in a Bode plot. As is evident in FIG. 8, the optimal sampling frequency depends not only on the immittance function being used but also on the specific construction and chemical characteristics of the interface. In FIG. 8A, for example, it is evident that 1 Hz is the best frequency to track the target binding at some modified electrode in the construction of an analytical curve based on Z'. At an interface equally and selectively receptive to the same target but prepared with a different receptor, the optimal frequency is 0.1 Hz (FIG. 8B).

FIG. 8A shows overlaid Bode complex impedance plots of a CRP receptive interface at different concentration of target. The optimal sampling frequency (from which analytical curves can be generated) is 1 Hz here. For a different CRP responsive interface the optimal frequency is 0.1 Hz (right).

The optimal sampling frequency can be obtained for any marriage of immittance function, interface and target through an automated software procedure. Once this has been established, analyses need only be carried out at that specific (optimized) frequency.

Using Relationships Between Immittance Functions Components

The methods described above outlined is not limited to just the matrix of functions listed in Table I but can also be extrapolated to almost "unlimited" combinations of immittance functions or real and imaginary derived terms. For instance, although the real and imaginary (not shown) components of the C* transfer function are shown to be largely unresponsive to the specific CRP target at the sensory interfaces referred to earlier, (Table II and III), combinations of C" and C', known as a tan δ function, can be effectively and sensitively utilized (see FIG. 9). It is additionally noteworthy that, in using function ratios in this way, target concentration is mapped in a linear, as opposed to logarithmic, manner.

Figure 9:
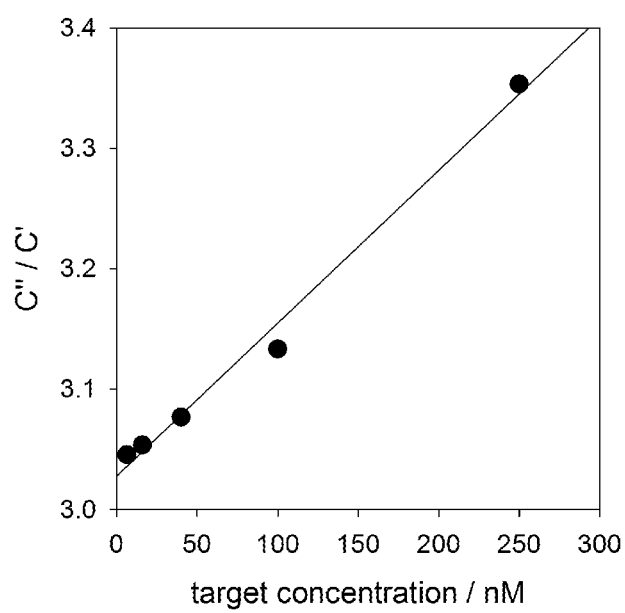
FIG. 9 shows a linear analytical curve of maximum value of C"/C' ratio function versus target concentration. The linear dependence of the Pearson coefficient is >98%. Note also that the ratio of C"/C' has no physical unit and a physical interpretation of this relationship is not necessary in its utilisation.

FIG. 9 shows linear analytical curve of maximum value of C"/C' ratio function versus target concentration. The linear dependence of the Pearson coefficient is >98%. Note also that the ratio of C"/C' has no physical unit and a physical interpretation of this relationship is not necessary in its utilisation. Variations of the functions are ~12% across 250 nM CRP target range.

In summary, the immittance function approach as described above provides users with a vast and potentially (software) automated arsenal with which to probe interfacial change such as those generated by the binding of targets at suitable receptive surfaces. From the library of analytical curves generated, some will be found to be more sensitive and reliable probes than others or more suited to specific concentration ranges. In enabling a sampling of a library of immittance functions this submission teaches an ability to powerfully sample electrode surfaces (and thus sense at them) without any prior assumption on behalf of the end user.

Example 2—Novel Bioelectrochemical Analysis Using Immittance Functions

The ability to exchange electrons with the redox active sites of proteins and enzymes has not only shed light on fundamental life-sustaining processes but is also powerfully applied in the generation of derived biosensors based on enzymes. The glucose biosensor is one specific, and highly successful, example.

The present inventors show here that the complex capacitance immittance function can also be utilized in directly following electrochemical events (that is the electron transfer between surface immobilized biomolecules and the underlying electrode surface) with exceptionally high definition. This is especially powerful in bioelectronics where faradaic signals (from immobilized proteins or enzymes) can be low and difficult to resolve by standard electrochemical methods. At such interfaces, the immobilization is commonly on an intervening (supporting) self-assembled monolayer. Exemplified here with the protein azurin, the methodology is equally applicable to any surface immobilized bioelectronic system. In screening the magnitude of this function as the electrode surface potential is swept, one has direct access to a determination of the electrochemical half wave potential, electron transfer kinetics and a quantification of the molecular density present.

1-hexanethiol, 1-octanethiol, 1-decanethiol and 1-dodecanethiolwere purchased from Sigma-Aldrich. 11-ferrocenyl-1-undecanethiol was purchased from Dojindo Molecular Technologies, Japan. All were used without further modification. Tetrabutylammonium salts (perchlorate, hexafluorophosphate) HPLC pureethanol, dichloromethane and acetonitrile were used as received (Sigma). *Pseusomonas aeruginosa* azurin was kindly donated by Prof. Canters group (Leiden University, NL). All solutions were prepared in MilliQ water water (18.2 MΩ).

Polycrystalline Gold Disk Electrodes (GDE) (Cypress Gold, diameter 1 mm) were cleaned by mechanical and electrochemical polishing and immersed in 1 mM thiol solutions in HPLC-pure ethanol (overnight, room temperature). The electrodes were then rinsed with ethanol and water and dried under nitrogen. Azurin physisorption on hydrophobic SAM surfaces of (hexanethiol, octanethiol, decanethiol, dodecanethiol) was obtained by depositing for 30 min. an aliquote of 5 µL of 0.5 mM protein in 20 mM MES buffer at pH7.0. The so-modified electrodes were then rinsed copiously with buffer and immersed in the electrochemical cell for analysis.

Cyclic Voltammetry (CV) and impedance measurements were carried out using an Autolabpotentiostat GSTAT20 (Ecochemie NL) equipped with an ADC750 and a FRA (frequency response analyses) module. Cyclic voltammograms were acquired only with the purpose of comparisons between the two methodologies. Single CV sweeps were also performed to pre-define faradaic windows prior to EIS analysis (required only if the redox potentials are not known prior). The AC frequencies for impedance experiments ranged from 1 MHz to 10 mHz, with an amplitude of 10 mV. The complex $Z^*(\omega)$ (impedance) function was converted into $C^*(\omega)$ (capacitance) through the physical definition $Z^*(\omega)=1/j\omega C^*(\omega)$ in which $\omega$ is the angular frequency. CVs and EIS scans were measured in a 5 mL, one compartment cell, containing the GDE, a saturated calomel reference (SCE) and a platinum gauze as counter electrode. As a supporting electrolyte, 200 mM $NaClO_4$ and 5 mM MES, buffered at pH 5.0 with NaOH, was used. All the solutions used for electrochemistry were deoxygenated by bubbling with ultrapure argon and purging the surface of the electrolyte for the duration of the experiment. Impedance data were acquired at fixed potentials of −200 mV and 90 mV vs. SCE, with modulation frequencies were varied in 80 steps from 0.1 mHz to 10 MHz.

Figure 10A:
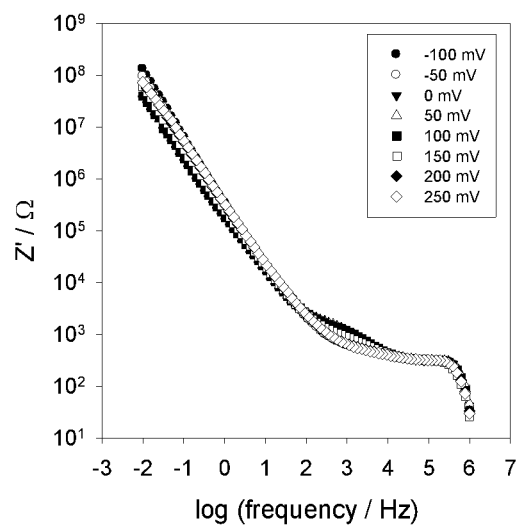
FIGS. 10A and 10B show, respectively, overlaid potential energy of the Bode complex impedance real and imaginary diagrams of an electroactive protein film on a SAM modified gold electrode showing a potential dependence which is negligible.
Figure 10B:
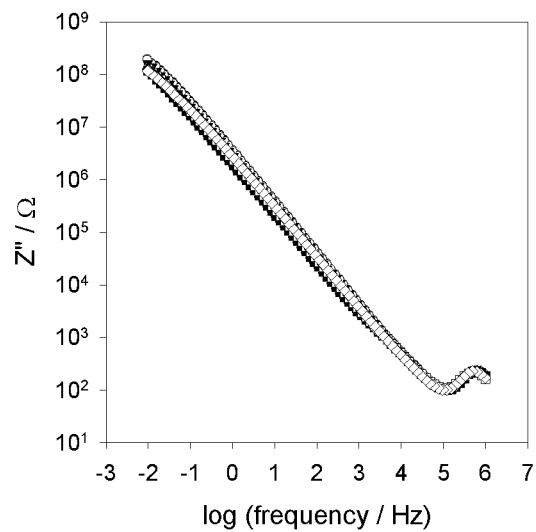

First we show that the impedance response of such bioelectronics interfaces is insensitive to the electrode potential (see FIGS. 10A and 10B). FIG. 10A shows overlaid potential energy of the Bode complex impedance real and FIG. 10B shows imaginary diagrams of an electroactive protein film on a SAM modified gold electrode showing a potential dependence which is negligible.

Figure 11A:
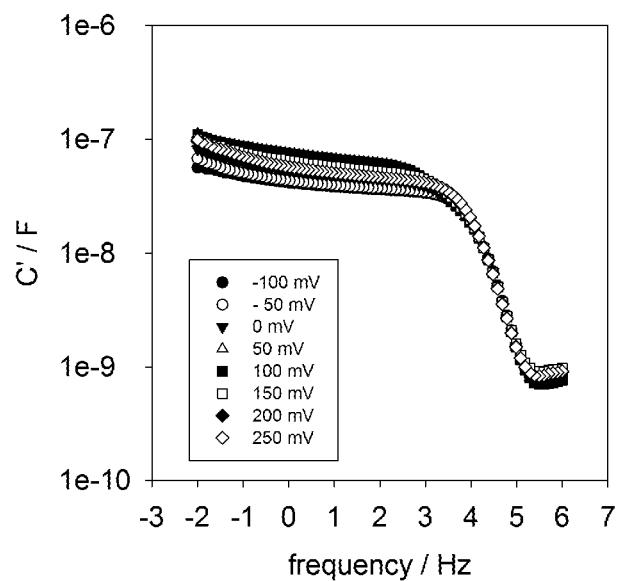
FIG. 11 shows overlaid Bode complex capacitive (real component, left, imaginary, right) diagrams of an azurin electroactive protein film as a function of electrochemical potential energy (i.e. from −100 mV versus SCE reference electrode to 250 mV).
Figure 11B:
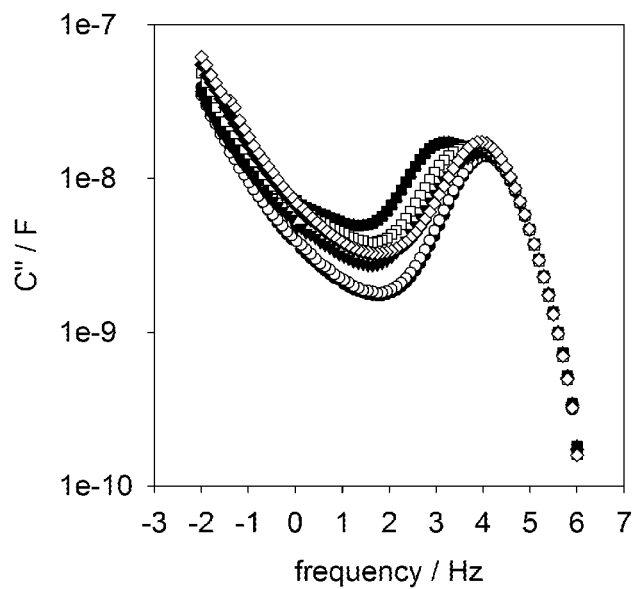

FIGS. 11A and 11B show overlaid Bode complex capacitive (real component, in FIG. 11A, imaginary component in FIG. 11B) diagrams of an azurin electroactive protein film as a function of electrochemical potential energy (i.e. from −100 mV versus SCE reference electrode to 250 mV).

Figure 12:
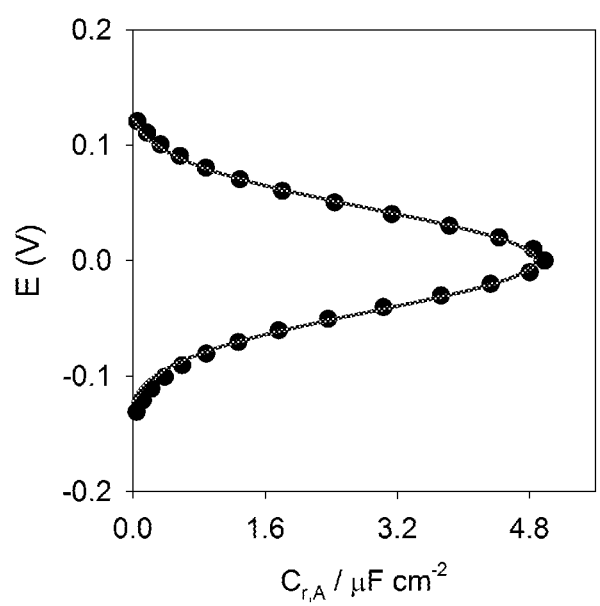
FIG. 12 shows a plot of redox capacitance ($C_r$) versus potential for an electrochemically active protein film. The plot is centred at zero here for convenience.

Notably, if one analyses the complex immittance function, $C^*$ (and thereafter its real and imaginary components) as a function of potential one resolves marked changes with surface potential (FIG. 11) across a broad range of sampling frequencies. The impedance derived complex capacitance immittance function does, then, report sensitively on the process of electron transfer. In the absence if electrochemistry this dependence vanishes. The use of the immittance function $C^*$ to study electrochemistry in this way is without precedent. If one analyses this "redox capacitance" (labeled as Cr here) as a function of electrode potential in more detail, the degree to which it reports on electrochemistry is clear (FIG. 12). A Gaussian dependence on potential is observed, with Cr maximum at the electrochemical reversible potential. The area under this curve directly reports the amount of electrochemically active material being addressed by the electrode.

FIG. 12 shows a plot of redox capacitance ($C_r$) versus potential for an electrochemically active protein film. The plot is centred at zero here for convenience.

In conclusion, the present inventors have shown a new way of communicating with electroactive films. Though exemplified with a redox protein film (where the signal: noise advantages are particularly advantageous), the methodology is equally applicable to any electroactive film and enables a facile resolution of reversible potential, electron transfer kinetics and molecular coverage.

Example 3—Extending the Linear Range

The present inventors consider that there is great value in extending the linear analytical range that is, by default, offered by an assay. They examined, through the use of multiple analytical functions, the potential of extending linear range with any given single receptive surface (of one fixed receptor-target binding affinity). This is illustrated in FIGS. 15 and 16, respectively (using one IF and 3 IF's, respectively).

Figure 15:
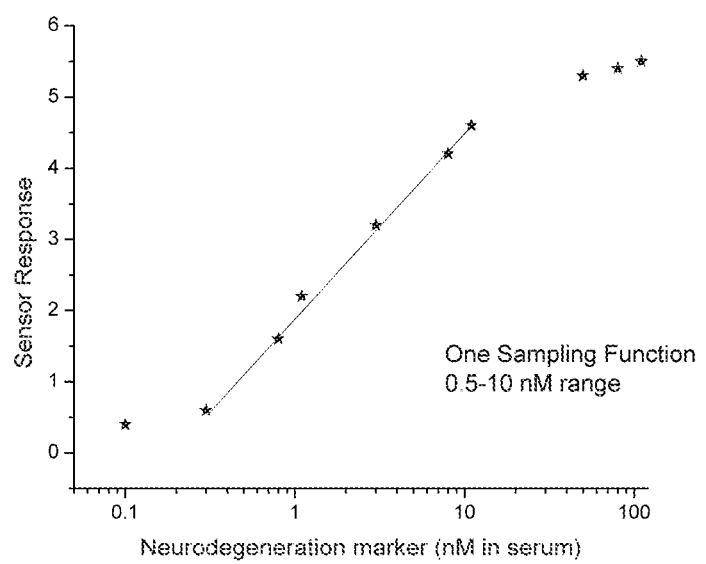
FIG. 15 shows a plot of M"/C" versus alpha synuclein autoantibody spiked into 50% blood serum. This graph results from a experiment carried out, which is described in Example 3 below.

FIG. 15 shows a plot of M"/C" versus alpha synuclein autoantibody spiked into 50% blood serum.

Figure 16:
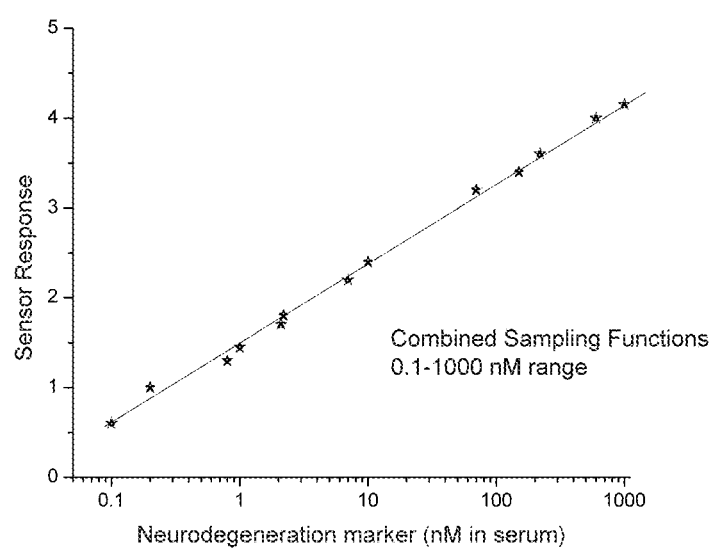
FIG. 16 shows a combination plot of Z"/C", M"/C" and M"/Y" versus alpha synuclein autoantibody spiked into 50% blood serum.

FIG. 16 shows a combination plot of Z"/C", M"/C" and M"/Y" versus alpha synuclein autoantibody spiked into 50% blood serum.

Experimental Details for Example 3

The receptive interfaces were generated through the covalent modification of a polyethylene glycol (PEG) thiol HS—C11-(EG)3-OCH2-COOH self assembled monolayer (Prochimia Surfaces, Poland) with recombinant human alpha-synuclein (expressed in *E. coli* and purified as described previously—see V. N. Uversky, *J Biomol Struct Dyn*, 2003, 21, 211-234). Covalent modification was achieved through the use of 1-ethyl-3-(3-dimethylaminopropyl) carbodiimide (EDC) and N-hydroxysuccinimde (NHS) (purchased from Sigma Aldrich). Ultrapure water (18.2 MΩ/cm) was obtained from a Milli-Q system and used throughout. Phosphate buffered saline (PBS, 10 mM) with Tween-20 (PBST, 10 mM, pH 7.4) was prepared by dissolving PBS tablets (Sigma Aldrich) in water with 0.2% v/v Tween-20 added, and filtered using a 0.22 μm membrane filter. All other chemicals were of analytical grade. Electrochemical experiments were performed with an Autolab Potentiostat 12 equipped with an FRA2 module (Metrohm Autolab B.V.). A conventional three-electrode system with a gold disk working electrode (1.6 mm diameter, BASi), platinum wire counter electrode and a silver/silver chloride (Ag/AgCl, filled with 1.0 M KCl) reference electrode (CH Instruments) were used. All potentials are reported relative to this reference. Electrochemical impedance spectroscopy (EIS) spectra were recorded in the frequency range from 0.05 Hz to 10 kHz. The amplitude of the applied sine wave potential was 10 mV with the direct current potential set at 0.25 V (the $E_O$ of the redox probe used, 1.0 mM $Fe(CN)_6^{3-/4-}$). Pure alpha-synuclein antibody was spiked into 50% diluted (with PBST (10 mM, pH 7.4)) commercially available serum (Sigma Aldrich) across a broad and quantified range (0.1 nM-1200 nM). Receptor modified electrodes were then incubated in these solutions additionally containing 1.0 mM $Fe(CN)_6^{3-/4-}$ at room temperature for 20 min, and EIS responses were recorded in the same incubation solution. To initially evaluate interfacial selectivity BSA was used and measured similarly.

Used biosensors were regenerated using a flow cell (1 mL volume with a flow rate of 3 mL/min) with 0.5 M glycine/HCl for 10 min prior to PBST washing. M", C", Z" and Y" function data was acquired from raw data as previously detailed. All data points plotted in FIGS. 15 and 16 are the means of repeats at 3 different receptor electrodes at that target concentration.

We claim:
1. An electrochemical test method comprising:
    (i) carrying out an electrochemical first step using an electrochemical apparatus controlled by a computer, wherein the first step involves applying an alternating potential or alternative current to a working electrode in a first physical environment over a plurality of concentrations for a target species and at a plurality of applied frequencies of applied current or applied voltage, respectively, monitoring the response of the electrode in terms of, respectively, the output alternating current or output alternating potential, and using a relationship between the applied alternating potential or alternating current and, respectively, the output alternating current or output alternating potential, calculating using a computer program a plurality of immittance functions and/or components thereof for each of the concentrations of the target species in the first physical environment and at each applied frequency of applied current or applied voltage, and determining, using the computer program, a quantitative relationship between each immittance function/component thereof and the concentration of a target species in a carrier medium at each applied frequency of applied current or applied voltage, the plurality of immittance functions forming a library of immittance functions, and the plurality of immittance functions being at least two of a complex impedance function, a complex admittance function, a complex modulus function, a complex dielectric constant transfer function and a complex conductance transfer function;

(ii) selecting from the library of immittance function, using a computer program, an immittance function or component thereof and a frequency of applied current or applied voltage for use in a subsequent electrochemical test, the selecting comprising:

comparing using a computer program how each immittance function or component thereof vary with a change in the concentration of a target species in a carrier medium for a first physical environment at each applied frequency of applied current or applied voltage and selecting using a computer program the immittance function or component thereof and the frequency of applied current or applied voltage, that together have the highest extent of variation with the change in concentration or the immittance function or component thereof and the frequency of applied current or applied voltage, that together have the highest correlation with the change in concentration;

(iii) carrying out a second electrochemical step using an electrochemical apparatus controlled by a computer, the second step involving:

applying an alternating potential or alternating current to a working electrode at a frequency selected in step (ii) in a second physical environment containing the target species, and monitoring, respectively, the response of the electrode in terms of, respectively, the output alternating current or output alternating potential, and, using a relationship value between the applied alternating potential or alternating current and, respectively, the output alternating current or output alternating potential, to calculate, using a computer program, a value for the selected immittance function or component thereof for the second physical environment, and using the qualitative relationship between the selected immittance function and component thereof determined in the first electrochemical step, calculating using a computer program, the concentration of the target species in the second physical environment, wherein the first physical environment provides a suitable system for calibrating the concentration of a target species in a carrier medium for the second physical environment; and wherein the carrier medium of the second physical environment comprises a biological fluid sample.

2. The electrochemical test method according to claim 1, wherein the at least one component of each immittance function is selected from the group consisting of: the real part of the immittance function, the imaginary part of the immittance function, the amplitude of an immittance function, the phase of the immittance function, and combinations thereof.

3. The electrochemical test method according to claim 1, wherein the method involves determining a first immittance function for the first physical environment and then generating for the first physical environment one or more second immittance functions from the first immittance function, and then determining how the first and one or more second immittance functions and/or components thereof vary with the concentration of a target species in a carrier medium.

4. The electrochemical test method according to claim 3, wherein the generating of the one or more second immittance functions from the first immittance function for the first physical environment involves using a phasorial analysis.

5. The electrochemical test method according to claim 1, wherein the method involves determining a first immittance function for the first physical environment, which is an impedance immittance function, determining one or more second immittance functions other than an impedance immittance function for the first physical environment, and then determining how the first and one or more second immittance functions and/or the components thereof vary with the concentration of a target species in a carrier medium.

6. The electrochemical test method according to claim 1, wherein the comparing comprises of at least one of:
(i) comparing the extent of variation of the immittance functions and/or components thereof with the change in the concentration of a target species in a carrier medium; and
(ii) comparing the correlation of the variation of the immittance functions and/or components thereof with the concentration of a target species in a carrier medium.

7. The electrochemical test method according to claim 1, wherein the determining involves plotting a component of each immittance function against either the concentration of a species in a carrier medium in the first physical environment or the logarithm of the concentration of a species in a carrier medium in the first physical environment.

8. The electrochemical test method according to claim 1, wherein the working electrode has on a surface thereof probe moieties that bind to the target species.

* * * * *